(12) United States Patent
Pan et al.

(10) Patent No.: US 10,400,262 B2
(45) Date of Patent: Sep. 3, 2019

(54) ANALYTE SENSING FOR EYE INJURIES AND CONDITIONS

(71) Applicants: The Board of Trustees of the University of Illinois, Urbana, IL (US); Carle Health Care Incorporated, Urbana, IL (US)

(72) Inventors: Dipanjan Pan, Champaign, IL (US); Santosh Kumar Misra, Urbana, IL (US); Manas Ranjan Gartia, Urbana, IL (US); Leanne T. Labriola, Champaign, IL (US)

(73) Assignees: The Board of Trustees of the University of Illinois, Urbana, IL (US); Carle Health Care Incorporated, Urbana, IL (US)

( * ) Notice: Subject to any disclaimer, the term of this patent is extended or adjusted under 35 U.S.C. 154(b) by 29 days.

(21) Appl. No.: 15/562,647

(22) PCT Filed: Apr. 1, 2016

(86) PCT No.: PCT/US2016/025507
§ 371 (c)(1),
(2) Date: Sep. 28, 2017

(87) PCT Pub. No.: WO2016/161255
PCT Pub. Date: Oct. 6, 2016

(65) Prior Publication Data
US 2018/0105857 A1     Apr. 19, 2018

Related U.S. Application Data

(60) Provisional application No. 62/141,487, filed on Apr. 1, 2015.

(51) Int. Cl.
*C12Q 1/00* (2006.01)
*G01N 33/50* (2006.01)
(Continued)

(52) U.S. Cl.
CPC ............... *C12Q 1/005* (2013.01); *C12Q 1/00* (2013.01); *G01N 27/3278* (2013.01);
(Continued)

(58) Field of Classification Search
CPC ..................... G01N 33/487; G01N 33/48707; G01N 33/50
See application file for complete search history.

(56) References Cited

U.S. PATENT DOCUMENTS 5,496,453 A   3/1996  Uenoyama
8,679,772 B2  3/2014  Gao
(Continued)

FOREIGN PATENT DOCUMENTS

SU        1571505 A1 *  6/1990
WO    2010/111484 A1    9/2010

OTHER PUBLICATIONS

Lei et al., Journal of Biotechnology, vol. 128, No. 1, Jan. 2007, p. 112-119. (Year: 2007).*
(Continued)

*Primary Examiner* — Eli S Mekhlin
(74) *Attorney, Agent, or Firm* — McDonnell Boehnen Hulbert & Berghoff LLP

(57) ABSTRACT

A biosensor for the detection of an analyte such as ascorbic acid is provided. Also provided is a device comprising the biosensor. In addition, methods of detecting analytes such as ascorbic acid in a sample, and methods of a point-of-care diagnosis of eye disease and eye injury are provided.

20 Claims, 20 Drawing Sheets

(51) Int. Cl.
*G01N 27/327* (2006.01)
*G01N 33/487* (2006.01)
*B82Y 15/00* (2011.01)

(52) U.S. Cl.
CPC ....... *G01N 33/48707* (2013.01); *G01N 33/50* (2013.01); *B82Y 15/00* (2013.01); *G01N 2333/90235* (2013.01); *G01N 2800/16* (2013.01)

(56) References Cited

U.S. PATENT DOCUMENTS

| | | | |
|---|---|---|---|
| 2002/0072084 A1* | 6/2002 | Meserol | C12Q 1/001 435/26 |
| 2004/0256685 A1* | 12/2004 | Chou | B22D 17/14 257/414 |
| 2006/0021881 A1 | 2/2006 | Soundarrajan | |
| 2006/0142651 A1 | 6/2006 | Brister | |
| 2008/0073208 A1* | 3/2008 | Wang | G01N 33/48771 204/406 |
| 2009/0165876 A1 | 7/2009 | Atkin | |
| 2010/0116691 A1 | 5/2010 | Papadimitrakopoulos | |
| 2011/0287468 A1 | 11/2011 | Yuan | |
| 2013/0252179 A1 | 9/2013 | Senzaki | |
| 2014/0371558 A1 | 12/2014 | Etzkorn | |
| 2015/0005186 A1 | 1/2015 | Huang | |

OTHER PUBLICATIONS

International Search Report for corresponding PCT application No. PCT/US2016/025507, dated Jun. 27, 2016.
Gartia et al., "Point-of-service, quantitative analysis of ascorbic acid in aqueous humor for evaluating anterior globe integrity", Scientific Reports, 5(1):1-14 (2015).
Choy et al., "Water-souble antioxidants in human tears: Effect of the collection method", Investigative Opthalmology & Visual Scient, 42(13):3130-3135 (2001).
Supplemental European Search Report for corresponding application No. 16774293.1, dated Aug. 23, 2018.

* cited by examiner

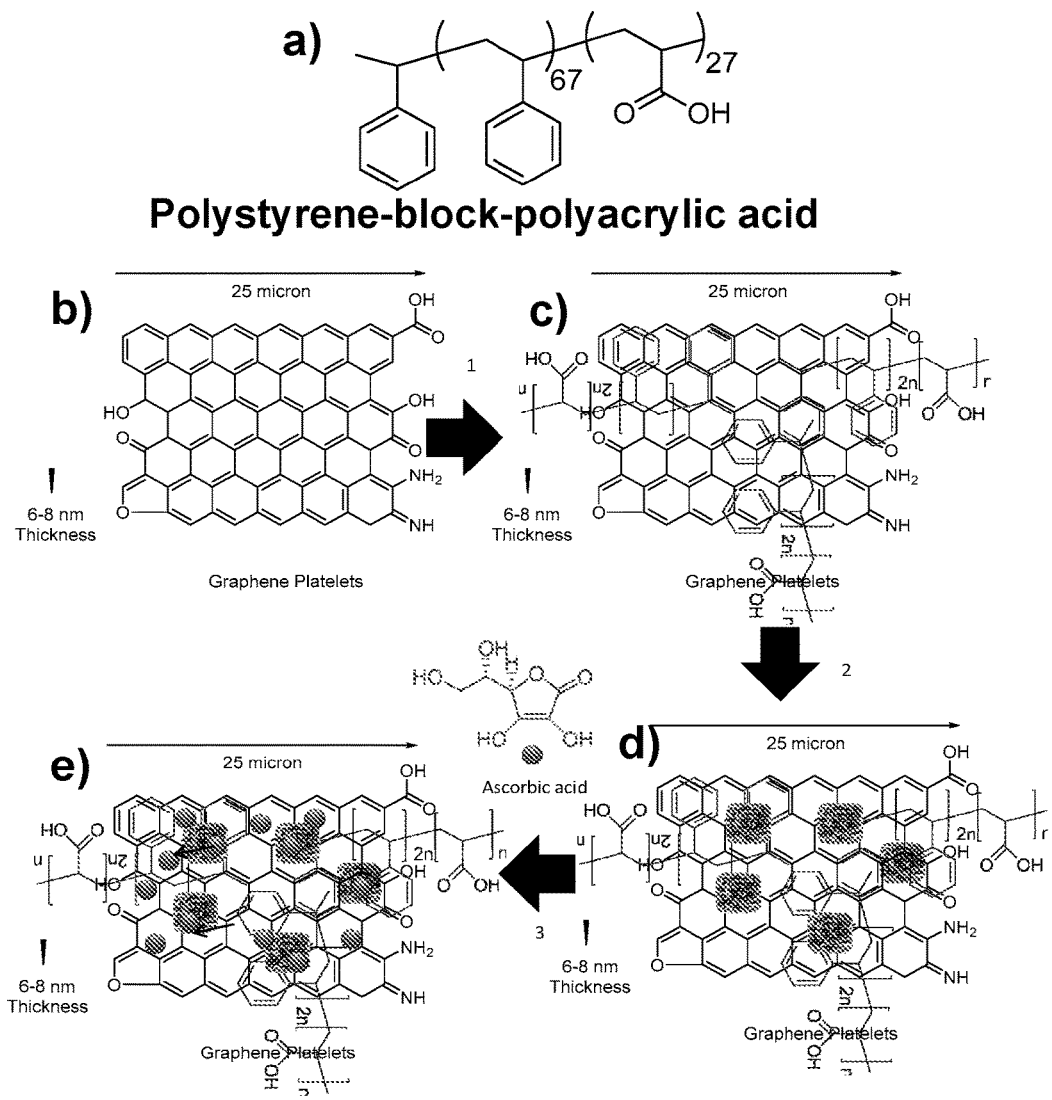
FIGS. 1 A-E

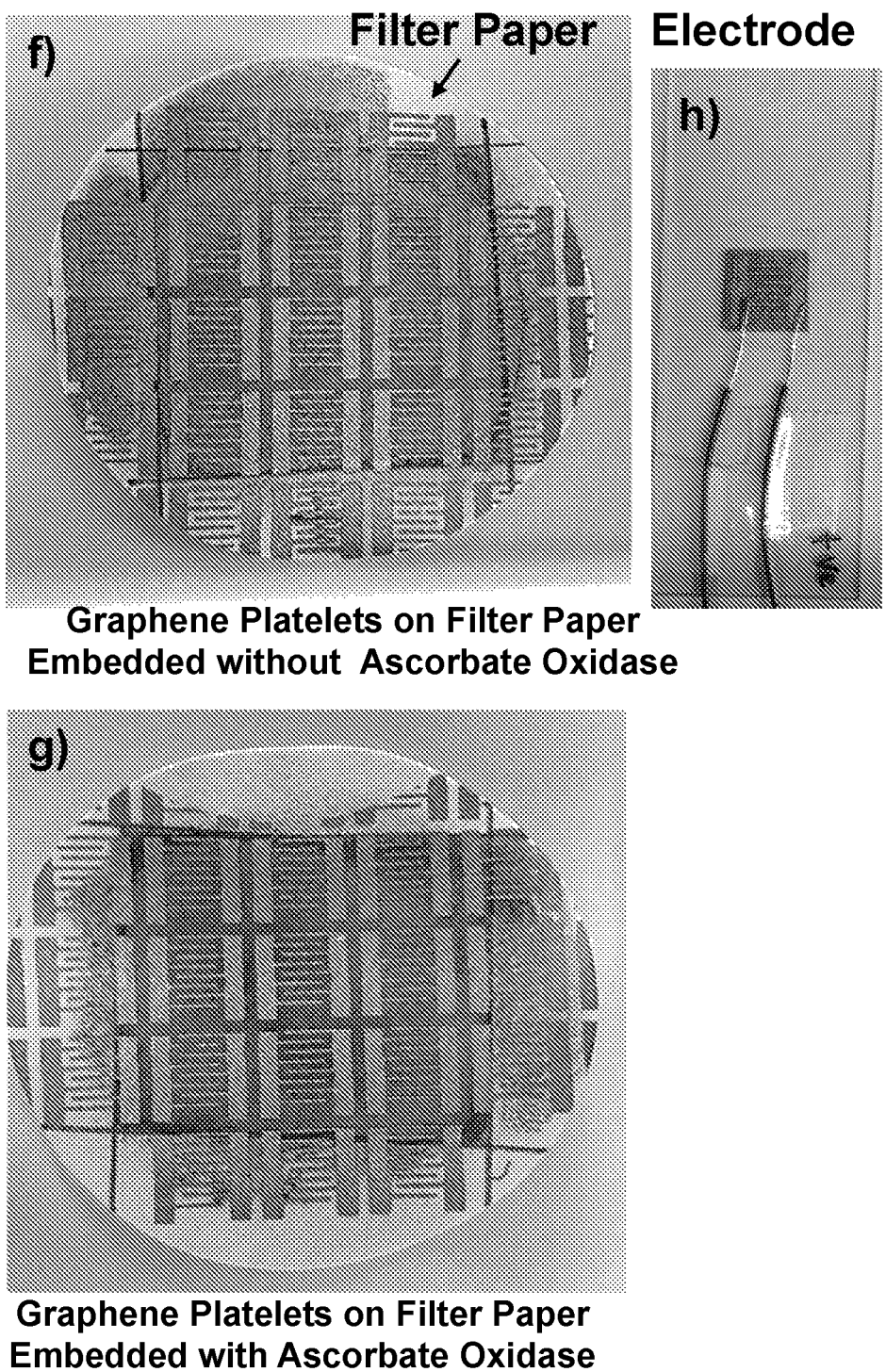
FIG. 1 F-H (A)

(B)

→ Extra Coating of Ascorbate oxidase
Magnification ──────────────

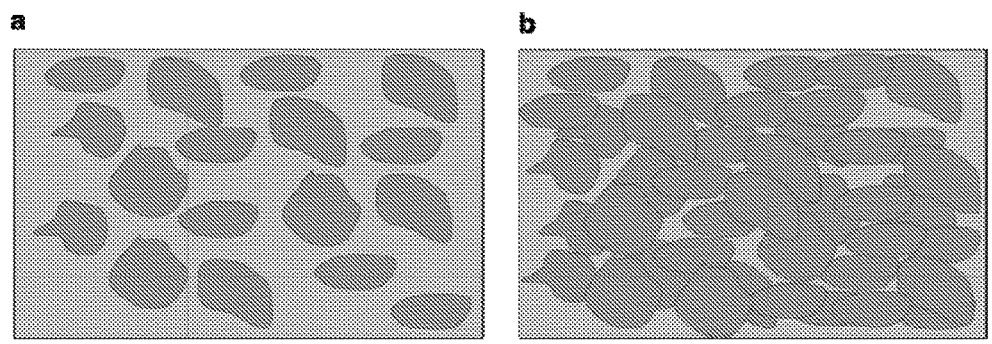
FIG. 3 A-B
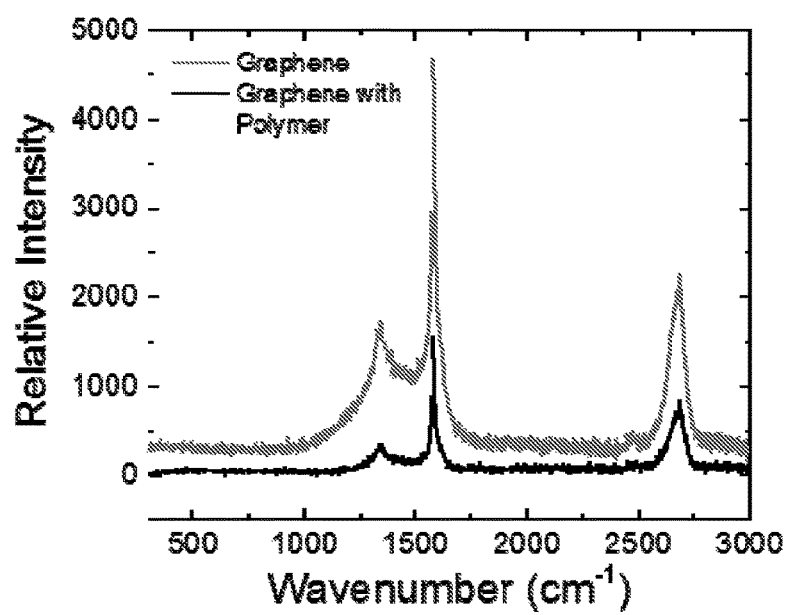
FIG. 4

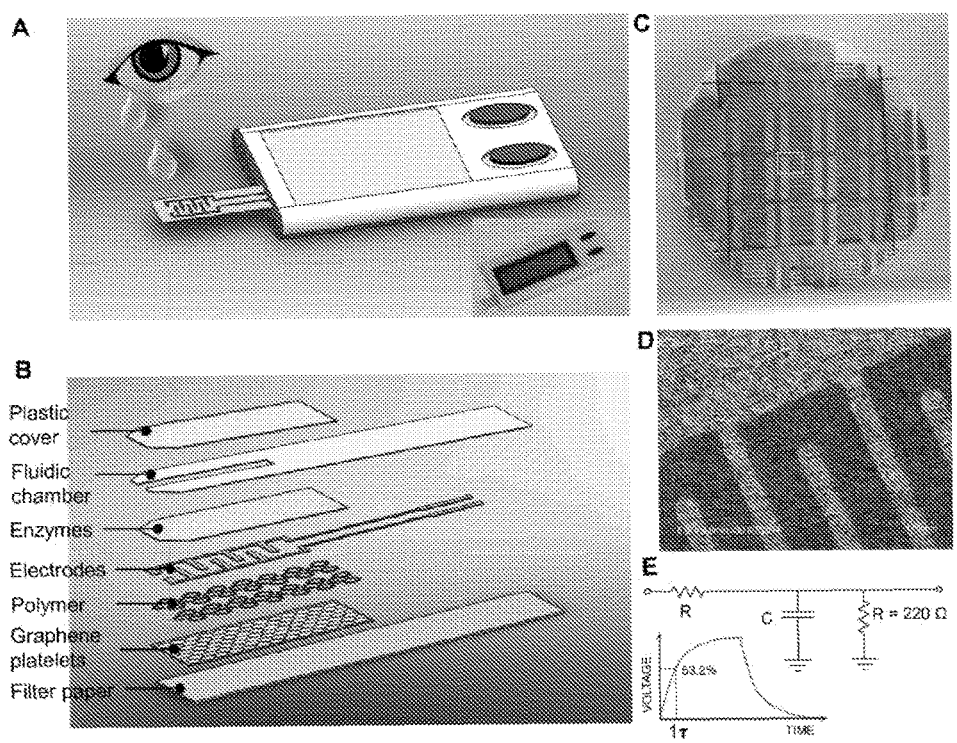
FIG. 10 A-E

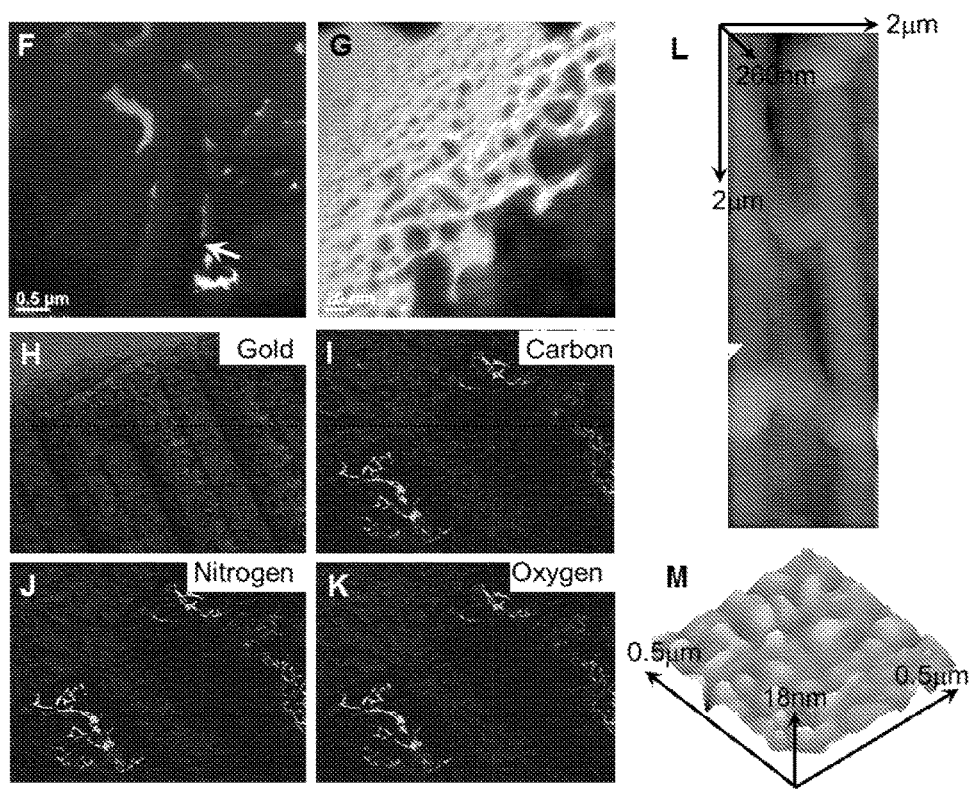
FIG. 10 F-M

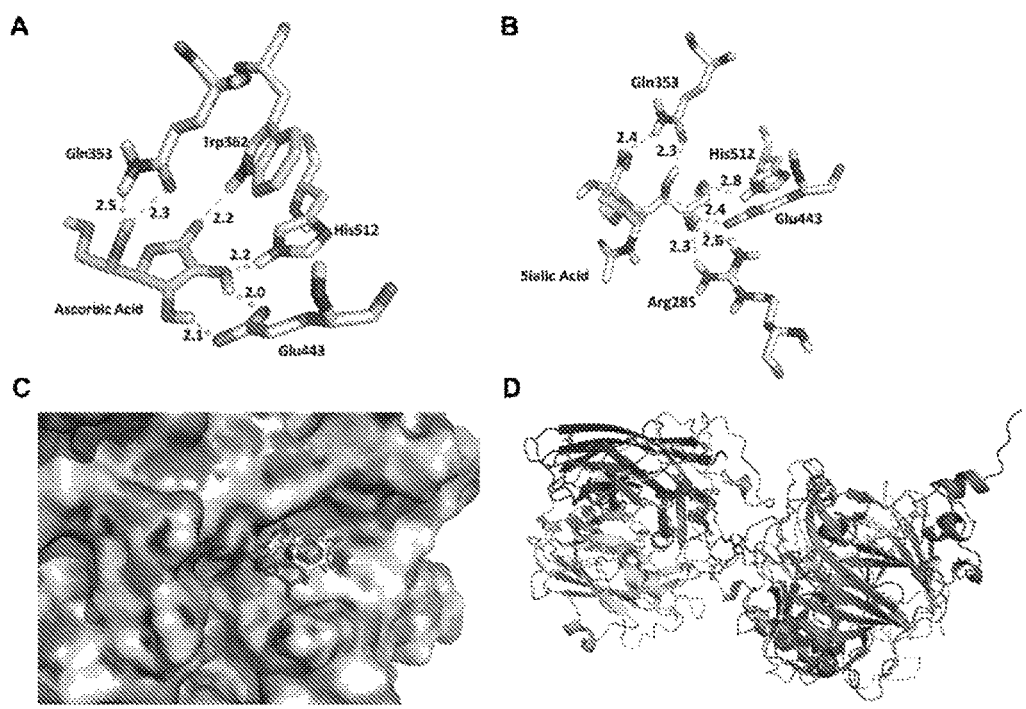
FIG. 11 A-D

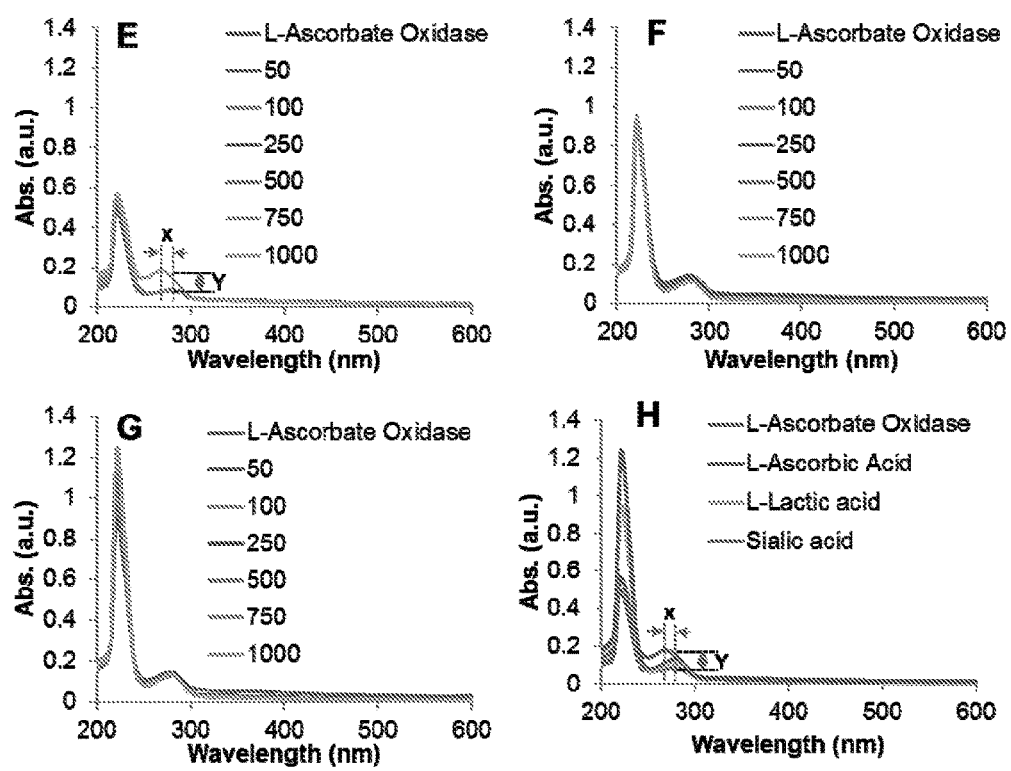
FIG. 11 E-H

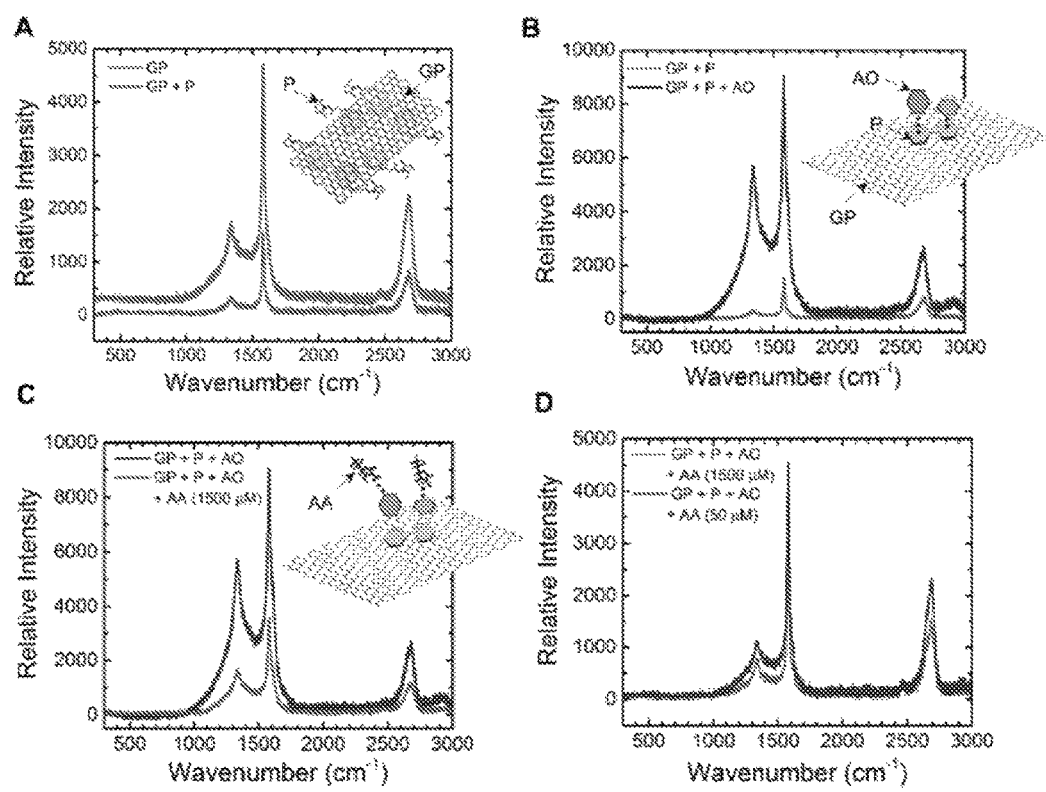
FIG. 12 A-D

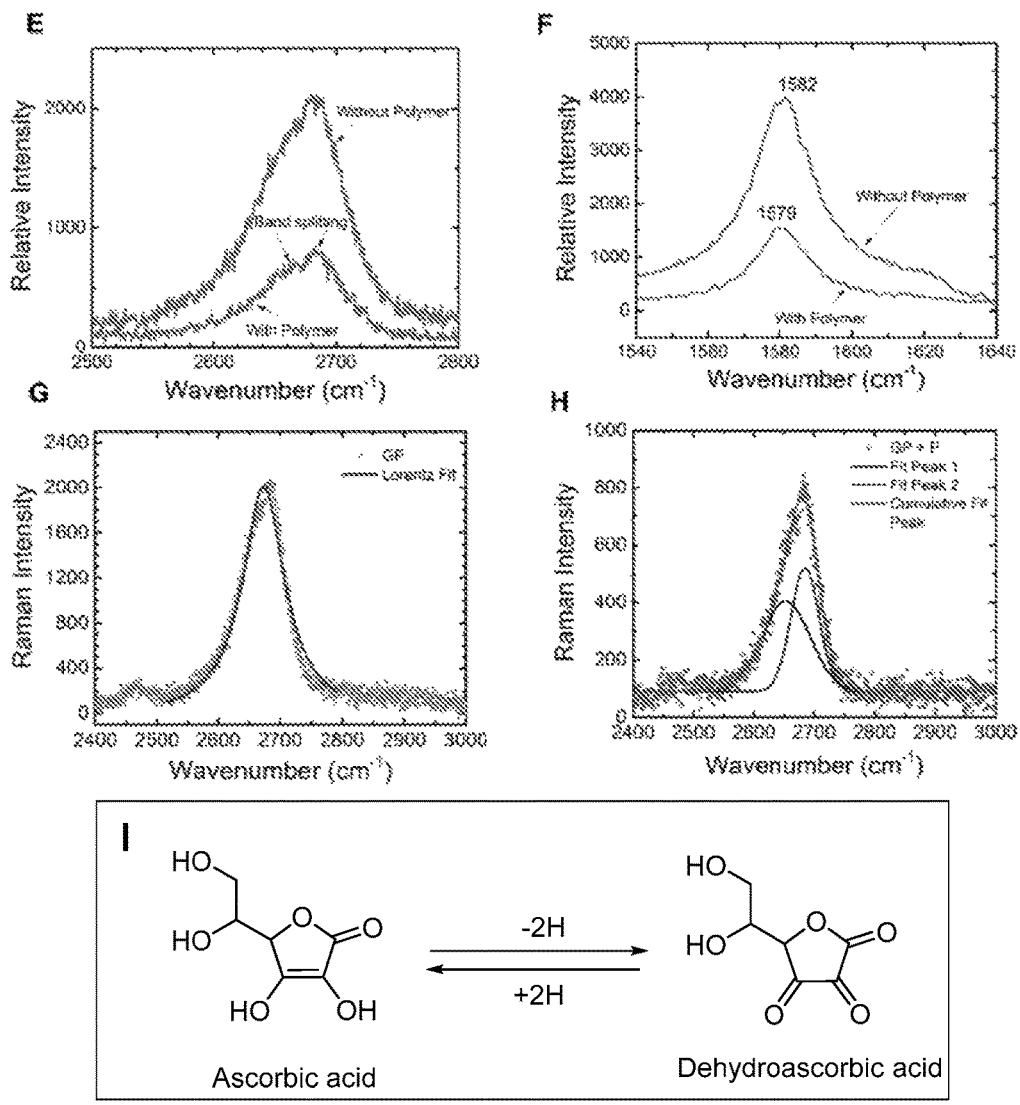
FIG. 12 E-I

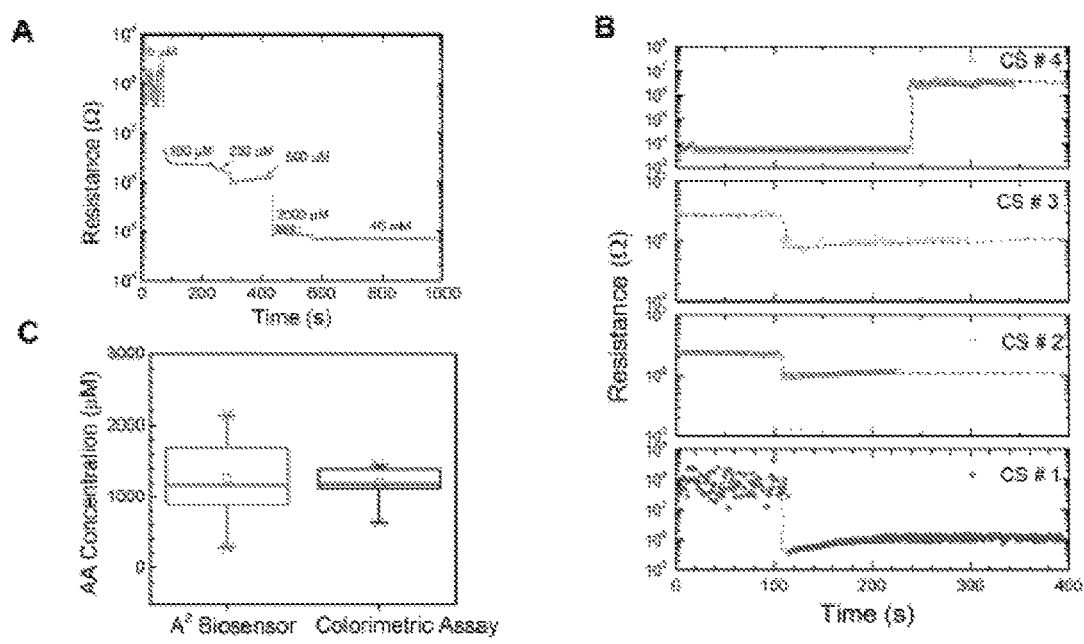
FIG. 13 A-C

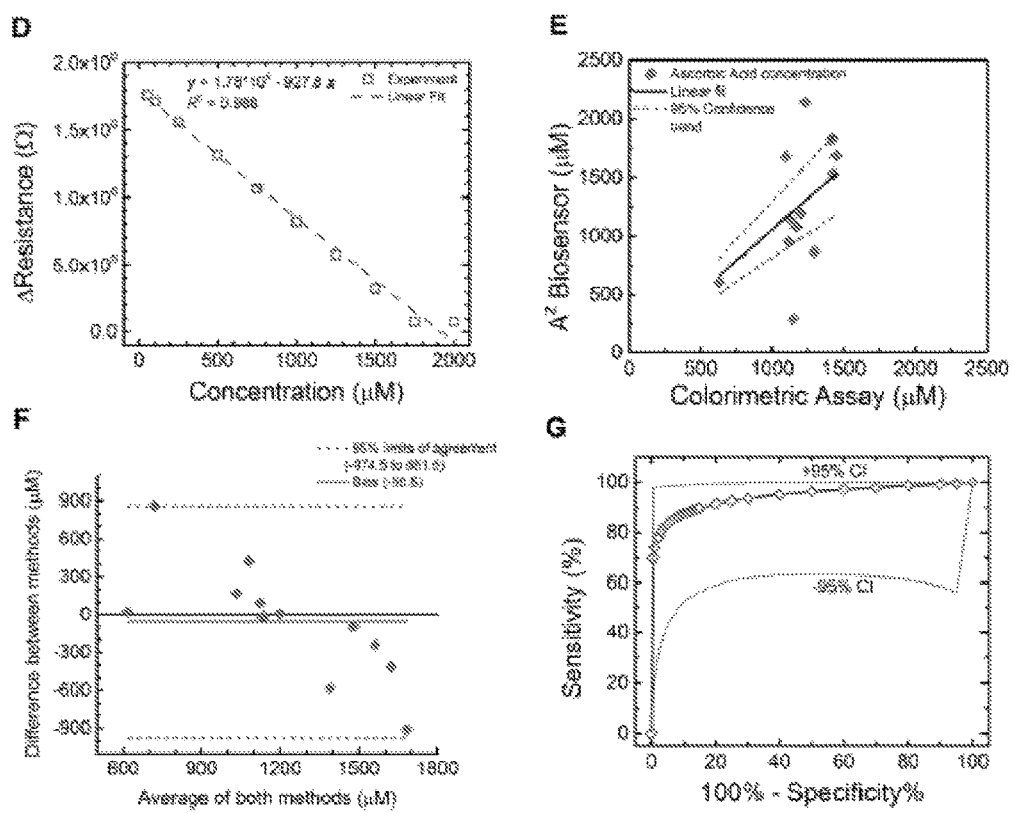
FIG. 13 D-G

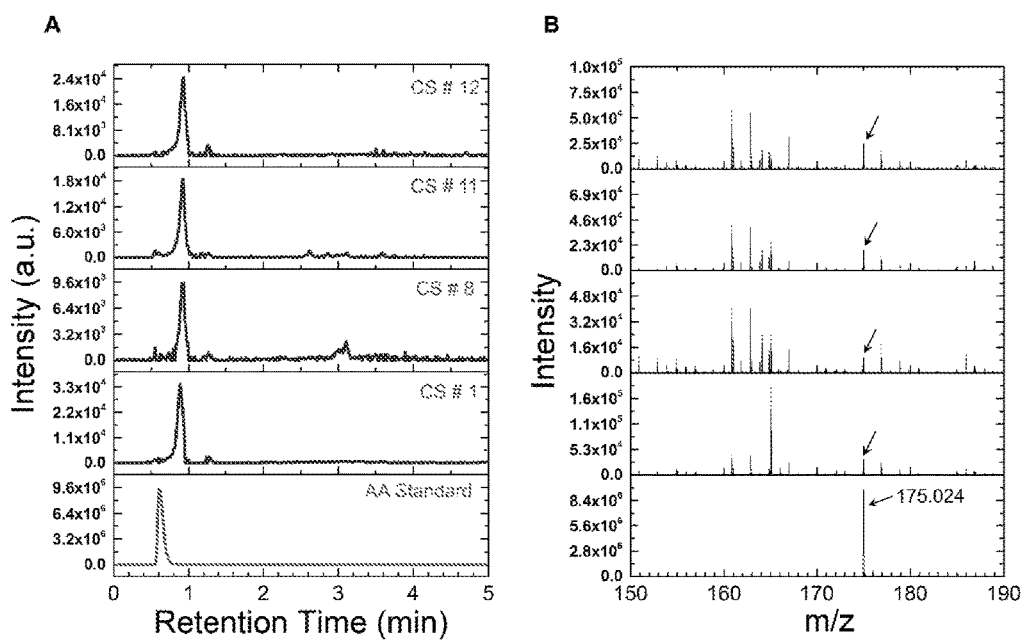
FIG. 14 A-B

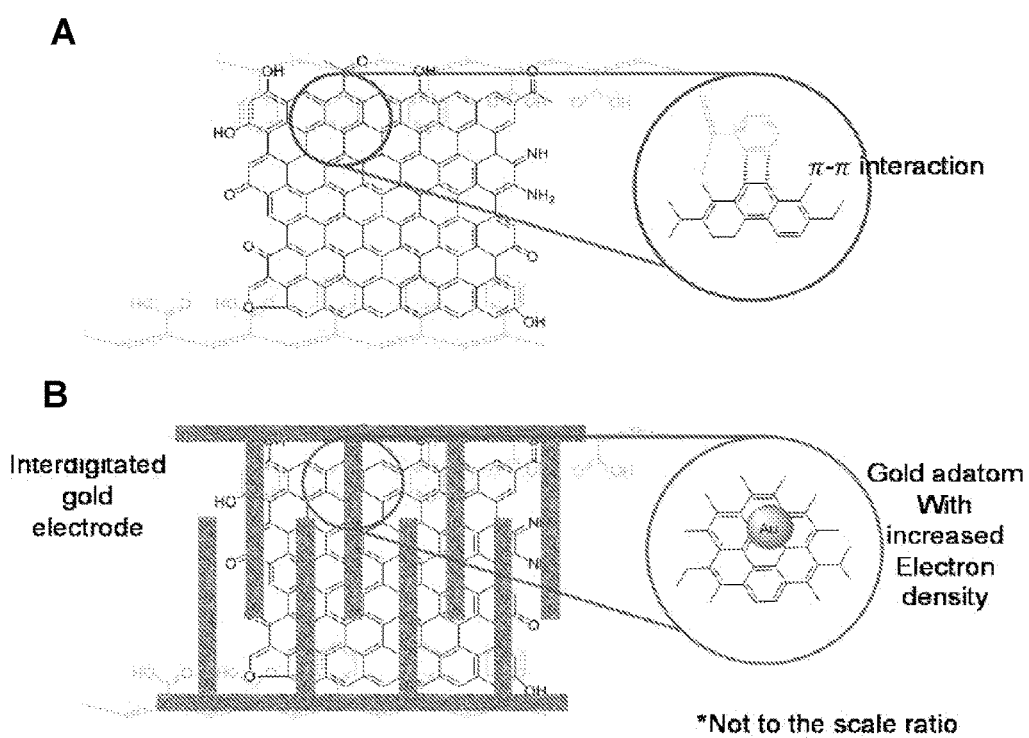
FIG. 15 A-B

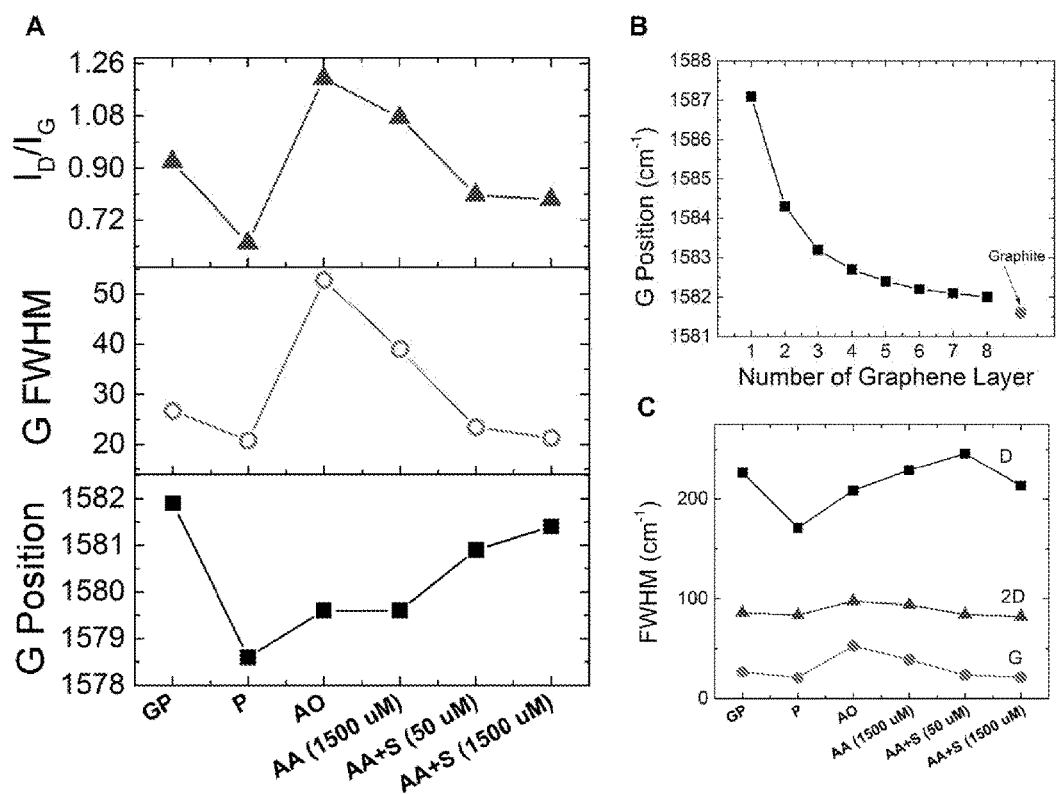
Fig. 16 A-C

ANALYTE SENSING FOR EYE INJURIES AND CONDITIONS

PRIORITY

This application claims the benefit of U.S. Ser. No. 62/141,487 filed on Apr. 1, 2015, which is incorporated by reference herein in its entirety.

BACKGROUND

Eye injuries and ocular complications present to many health care professionals through emergency department visits, convenient care appointments or primary care evaluations; however, accurate ocular examination typically requires specialty training and expert knowledge of the use of ophthalmic diagnostic equipment such as the slit lamp biomicroscope. The limited instruction available on these devices and restricted access to the equipment due to the high cost and immobility, inhibit the ability for primary care providers to adequately diagnose, triage, or manage complicated ocular conditions. This is particularly problematic when cases of serious ocular injuries, that require urgent attention, present outside of an ophthalmology office. This occurs in patients with a suspected ruptured globe or post-operative infections.

Current methods for evaluating the integrity of the anterior globe in trauma patients and the wound integrity in post-operative patients involve the use of the Seidel Test. This test is performed by placing a high concentration of fluorescein dye into the ocular tear film and then observing for a change in the color of the dye. The change in color would indicate the passage of aqueous humor through a corneal or anterior scleral wound, which represents a direct communication of the internal eye fluid with the external tear film. The Seidel Test is subjective and not standardized, and the amount of pressure and technique used when performing this test varies between clinicians. Other devices that are used to aid in diagnosis of trauma patients include conventional X-ray, computed tomography (CT), ultrasound (US), and magnetic resonance imaging (MRI), but they are limited in their capability to detect eye injuries. Specifically, plain film radiographs have no utility in detecting soft tissue injuries to the eye; CT images do not visualize small anterior lacerations to the cornea, and US is contraindicated with anterior globe ruptures. In addition, all of these imaging devices are expensive and are restricted to hospital settings due to their size and cost. Furthermore, none of these devices are available for evaluation of an eye trauma by first responders in the field or for military use in combat settings.

Compositions and methods are needed in the art for inexpensive, point of care diagnosis of eye injury and disease.

SUMMARY OF THE INVENTION

One embodiment of the invention provides a biosensor for the detection of an analyte. The biosensor comprises a layer of graphene nanoplatelets, carbon nanotubes, or fullerene, a layer of one or more polymers on the layer of graphene nanoplatelets, carbon nanotubes, or fullerene, a layer of a ligand for the analyte on the polymer layer, and at least one sensor electrode. The analyte can be present in a tear film. The at least one sensor electrode can be between the layer of one or more polymers and the layer of a ligand for the analyte. The analyte can be ascorbic acid and the ligand for the analyte can be ascorbate oxidase. The ascorbate oxidase can be present at a concentration at about 3 to about 100 $U/cm^2$. The biosensor can further comprises a substrate. A substrate can be selected from one or more of filter paper, acrylamide, cellulose, nitrocellulose, glass, silicon wafer, indium tin oxide, mica, polystyrene, or polyvinylidene fluoride (PVDF) filter, glass fiber filters, fiberglass, polyethylimine coated glass fiber filters, porous mylar, transparent porous film, cellulose nitrate (CN) membrane, mixed cellulose ester membrane, cellulose acetate membrane, polyethersulfone (PES) membrane, PTFE membrane, ultra-filtration membranes of poly(vinyl chloride) (PVC), carboxylated poly(vinyl chloride) (CPUC), polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. The one or more polymers can be poly(styrene) block-poly (acrylic acid) (PS-b-PAA). The biosensor can comprise a fluidics chamber and/or a cover.

Another embodiment of the invention provides a device comprising the biosensor of the invention and a detector connected to a data acquisition system. The detector can be a multimeter. The data acquisition system can be selected from the group consisting of a computer, a hand-held device, a cell phone, and a tablet. The device can further comprise a screen that allows for visualization of an amount of analyte present in a sample.

Still another embodiment of the invention provides a method of detecting an analyte in a sample comprising contacting a biosensor of the invention with the sample and detecting the analyte with a detector. The detector detects binding or interaction of the analyte and the analyte ligand due to a change in electrical resistance caused by binding or interaction of the analyte in the sample with the analyte ligand; due to a change in mass on the biosensor; due to a colorimetric change; due to a fluorescent reaction; due to a change in a Raman spectroscopy reading; due to a change in a Fourier transform infrared spectroscopy reading, due to a change in a mass spectrometry reading, or due to electrochemical changes.

Even another embodiment of the invention provides a method of detecting an analyte in a sample. The method comprises contacting a sample with a biosensor of the invention, and inserting the biosensor into or onto a device comprising a detector to measure change in electrical resistance, and a screen for visualizing the change in resistance, thereby detecting an analyte in the sample. The amount of the analyte in the sample can be detected. The sample can be tears, tear film, aqueous layer of the tear film, aqueous humor, sweat, blood, serum, plasma, urine, saliva, or other bodily fluids.

Another embodiment of the invention provides a method of diagnosing an eye condition. The method comprises contacting a biosensor of the invention with a tear, tear film, aqueous layer of the tear film, or aqueous humor sample of a subject, detecting an amount of an analyte in the sample, and diagnosing an eye condition in the subject where the concentration of the analyte in the sample is elevated as compared to a control sample or control standard. The eye condition can be selected from a full or partial thickness laceration or perforation to the anterior chamber of the eye, eye disease, mechanical or chemical eye injury, anterior scleral injury, corneal wound integrity, aqueous humor leaks, eye ulcer, infection, or surgical incisions.

Yet another embodiment of the invention provides a method of diagnosing an eye condition in a subject. The method comprises detecting the amount of ascorbic acid in a tear film sample from the subject and diagnosing an eye condition in the subject where the amount of ascorbic acid is elevated as compared to a control standard or control sample. The analyte can be ascorbic acid.

BRIEF DESCRIPTION OF THE DRAWINGS

The features, objects and advantages other than those set forth above will become more readily apparent when consideration is given to the detailed description below. Such detailed description makes reference to the following drawings, wherein FIG. 1. Composition of GRP-polymer composites and surface coated filter paper. (a) Polystyrene-b-Polyacrylic Acid (PS-b-PAA); (b) graphene platelets (GRP); (c) GRP-polymer coated filter paper and (d) ascorbate oxidase loaded GRP-polymer coated filter paper; (e) ascorbic acid bound biosensor; (f) graphene platelets on filter paper embedded without ascorbate oxidase; (g) graphene platelets on filter paper embedded with ascorbate oxidase; (h) arrangement for electrode connection with the biosensor.

FIG. 3. (a) Scenario when the concentration of graphene platelet is low (Type-I). (b) Scenario when the concentration of graphene platelet is high (Type-II).

FIG. 4. Raman spectra showing the graphene platelet and the graphene platelet with polymer layer.

FIG. 10. Schematic and operating principle of a biosensor device (A) Graphical schematic of biosensor and sample processing. The inset shows an image of the 3D printed cassette along with LCD screen and the biosensor. (B) A biosensor device can comprise interdigitated gold electrodes placed between layers of graphene platelets mixed with polymers, and ascorbate oxidase enzyme. The biosensor is laminated with polyester fluidic chamber and a cover. The whole structure is supported on a filter paper. (C) Optical image of the biosensor made on filter paper and the corresponding SEM image is shown in (D), (E) The circuit diagram used to measure the surface resistance of the biosensor. Surface characterization of biosensor strips using TEM. Representative TEM show the variation in (F) high coating and (G) low coating biosensor strips. (H-K) SEM/EDX analysis for the elemental map of biosensor chip for elements (H) gold; (I) carbon; (J) nitrogen and (K) oxygen, respectively. AFM analysis shows the representative (L) polymer coated fibers on paper biosensor and (M) height profile of platelets across biosensor strip.

FIG. 11. Computational and experimental study of binding affinity and selectivity of ascorbic acid (AA) to the enzyme coating a biosensor. (A) Docking pose of AA with 1AOZ. (B) Docking pose of sialic acid with 1AOZ. (C) Molcad surface picture of superimposition of AA and sialic acid docking poses, (D) Image showing AA bound to ascorbate oxidase. Selectivity of ascorbate oxidase toward ascorbic acid. Interaction study at various concentrations (50-1000 µM) of (E) L-ascorbic acid; (F) L-lactic acid and (G) sialic acid. (H) Comparison of interactions at 1000 µM showed only interactions of L-ascorbate oxidase with L-ascorbic acid with changes in Amax of absorption (x) and absorption maxima (y) while interactions with L-lactic acid and sialic acid showed no significant interaction.

FIG. 12. Surface characterization study using Raman spectroscopy to understand the layer-by-layer assembly of a biosensor and chemistry of enzymatic action. (A) Comparison of Raman spectra with and without polymer (P) layer on graphene platelets (GP). (B) Comparison of Raman spectra with and without ascorbate oxidase enzyme (AO) layer on polymer coated graphene platelets (GP+P), (C) Comparison of Raman spectra with and without ascorbic acid (AA) on polymer coated graphene platelets with enzyme layers (GP+P+AO). (D) The effect of concentration of AA on the Raman spectrum of GP+P+AO layers. (E) The result showing splitting of 2D-band of graphene after coating the graphene platelets with polymer. (F) The G-band of the graphene shifted to lower energy (wavenumber) after coating the graphene platelets with polymer. Results showing the single Lorezian curve fit to data obtained without polymer layer (G), and two Lorenzian curves to fit the peak obtained from graphene platelets with polymer layer (H). (I) Chemistry of ascorbic acid degradation by ascorbate oxidase to generate ehydroascorbic acid.

FIG. 13. Performance of a biosensor of the invention compared to colorimetric assay measuring ascorbic acid (AA). (A) Typical results obtained from a biosensor showing the concentration dependent resistance measurements. (B) Typical resistance measurements obtained from clinical samples on the biosensor. Here, four different clinical samples (labeled CS#1-4) are shown that are measured on four different paper-based biosensors. (C) Box plot showing the comparison of a biosensor of the invention and colorimetric assay using clinical samples (n=12) obtained from the aqueous humor of the eye. (D) Calibration curve of a biosensor using standard AA solution showing the linearity of the biosensor. (E) Comparison between a biosensor and colorimetric assay using clinical sample (n=12). The dashed lines represent the upper and lower 95% confidence interval (CI). The solid line is a linear fit to the data with the y intercept at 0. (F) Bland-Altman plot of results comparing the two methods. The dashed lines represent the upper and lower 95% confidence interval for the level of agreement. The solid lower curve represents a bias and the solid upper line (at 0) is the line of equality. (G) ROC curve along with the 95% CI curve is provided for a biosensor.

FIG. 14. LC chromatogram and HR-MS analysis of clinical samples. (A) LC/MS/MS Multiple Reaction Monitoring (MRM) analysis for AA standards and representative clinical samples (CS#1, 8, 11, 12). (B) Corresponding high resolution mass spectrometer (HR-MS) data of AA standard and clinical samples. The characteristic AA fragment is obtained at m/z of 175.024 (denoted by an arrow). The same peak is also seen in all the clinical samples (denoted by arrow) confirming the presence of AA in the samples.

FIG. 16. (A) Effect of stacking of polymer, ascorbate oxidase layer and subsequent interaction with ascorbic acid on the G band (position and line width, FWHM) of graphene, and the intensity ratio of D, and G-band of graphene. (B) Results showing the decrease of G-band energy due to increase of number of graphene layers. The G-band frequency can be fitted to the following equation, where n is the number of graphene layer:

$$\omega_G = 1581.6 + \left(\frac{11}{1+n^{16}}\right).$$

Figure 2A:
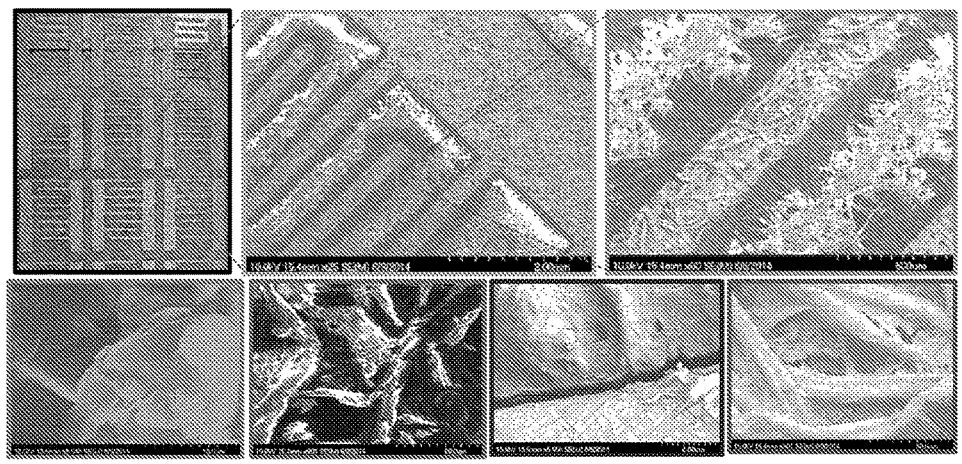
FIG. 2A. Schematic of biosensors and Scanning Electron Microscopy (SEM) images showing different components without ascorbate oxidase coating.

(C) The effect of stacking of polymer, ascorbate oxidase layer and subsequent interaction with ascorbic acid on the line width of D, 2D, and G-band of graphene.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments above and claims below for interpreting the scope of the invention.

DETAILED DESCRIPTION

There are currently no FDA-approved point-of-service (POS) tests that directly measure analytes such as ascorbic acid (AA) in tear film. Other methods of AA detection include HPLC, electrochemical, colorimetric, absorbance, and fluorescence measurement, but all of them have serious limitations of requirement of sophisticated instrumentation, limitation to low concentration detection, and extensive sample preparation. This is the first time that ascorbic acid has been identified as a biomarker for eye conditions.

The invention provides compositions and methods that provide an objective, reliable platform for testing of analytes such as ascorbic acid (AA) within the ocular tear film or other bodily fluids as a surrogate biomarker of for example, anterior scleral or corneal wound integrity, which could replace the subjective Seidel Test and provide more information than the Seidel Test since the device will provide an objective measurement that the Seidel test cannot provide. The biosensor can also be performed in point-of-care device that does not require patient positioning at a slit lamp. The only information that the Seidel provides is a subjective evaluation of the tear film. The biosensors of the invention are the first of their kind to provide objective information about the tear film composition including the detection of analytes and biomarkers in the tear film for sepsis or infection. The method utilizes the about 20-fold difference in AA concentrations found in ocular fluids. Aqueous humor has an average AA concentration of about 1049±433 micromol/L whereas the ocular tear film only has an average AA concentration of about 23±9.6 micromol/L. With this fundamental difference in concentration and the fact that aqueous humor is continuously produced within the anterior chamber, when the integrity of the anterior globe is disturbed from a laceration, the higher concentrations of AA from within the continuously flowing aqueous humor will be released into the tear film causing a rise in the amount of AA in the tear film that can be quantified. The tear film AA concentration can be detected and measured by compositions of the invention. AA has not previously been suggested as a biomarker for eye conditions.

The validity of the results obtained using compositions of the invention is shown by the strong correlation with the AA concentration obtained through standard colorimetric coupled enzyme reaction assay and mass spectrometric based analytical methods. The compositions can provide accurate AA concentration quickly (within 5, 4, 3, 2 minutes or less) using small sample sizes (about 0, 5, 1.0, 2, 5, 10 or 15 µL) of sample, suggesting laboratory quality data can be realized with this technique of using a battery-powered, handheld unit with disposable biosensor strips.

In one embodiment, compositions and methods of the invention involve the use of nanotechnology through an enzyme-graphene decorated plated electrode to quantitatively measure the concentration of tear film AA. An important feature of biosensors of the invention that sets it apart from current care options is the reporting of the level of analyte concentration on, for example, an electronic screen, making the results easy to read and suitable for use by a non-ophthalmologist.

The measurement provided by certain biosensor devices of the invention (e.g., a resistance-based measurement) can be performed in the clinical setting with an immediate result without having to send the samples to a laboratory for further sampling or analysis, as competing assays require. This feature of a biosensor enables clinical use due to the fact that analytes such as AA can rapidly degrade after collection. In previous studies L-ascorbic acid solution degraded during storage for longer periods in the presence of oxygen due to oxidation of AA. It involves the loss of two electrons and two protons while oxidation product dehydroascorbic acid ($C_6H_6O_6$) is relatively unstable in aqueous solution, since it spontaneously reacts with water to yield 2,3-diketogulonic acid. The rate of oxidation depends on the concentration of oxygen, temperature, enzyme or transition metal catalysis or basic pH abundance. The ability of compositions of the invention to test the tear film immediately avoids the problems that occur with oxidation and increases accuracy of the test. The disclosure presents examples of point-of-care biosensor devices, which can accurately and quantitatively measure analytes such as ascorbic acid levels in samples such as human tear film. The measurement of analytes such as ascorbic acid can be an important biomarker for the stability of the cornea integrity. A further benefit is an easy to use, hand-held, battery-powered device that can utilize disposable biosensor strips. Devices and methods of the invention can supplement clinical diagnosis and provide valuable information for first responders and quantitative, objective measurements for degree of injury.

Biosensor

Compositions of the invention include biosensors for the detection of analytes such as ascorbic acid. The biosensor can comprise a layer of graphene nanoplatelets, fullerene (such as $C_{60}$), or carbon nantotubes, a layer of one or more polymers on top of the layer of graphene nanoplatelets, fullerene, or carbon nanotubes, a layer of an analyte ligand (such and a ligand for ascorbic acid) on top of the polymer layer; and at least one sensor electrode. The at least one sensor electrode can be between the one or more polymers layer and the analyte ligand layer. A biosensor of the invention can further comprise a substrate.

The layer of graphene nanoplatelets, fullerenes, such as buckminsterfullerene, or carbon nantotubes can have a top surface and a bottom surface. A layer of one or more polymers can have a bottom surface and a top surface. A layer of a ligand for an analyte can have a top surface and a bottom surface. A sensor electrode and a substrate can each have a top surface and a bottom surface. A biosensor can have a layer of graphene nanoplatelets, fullerene, or carbon nanotubes. The bottom surface of the layer of one or more polymers can be deposited on the top surface of the graphene nanoplatelets, fullerene, or carbon nanotubes. The bottom surface of the analyte ligand layer can be deposited on the top surface of the polymer layer. The bottom surface of one or more electrodes can be present on the top surface of the polymer layer. The top surface of the one or more electrodes can be in contact with the bottom surface of the analyte ligand layer. The bottom surface of the graphene nanoplatelets, fullerene, or carbon nanotubes layer can be in contact and supported by the top surface of a substrate.

None of the layers need to be continuous. That is, the layer does not need to completely cover the layer upon which it rests. A layer can be 100%, 90%, 80%, 70%, 60%, 50%, or less continuous. For example, a layer covers or coats about 50%, 60%, 70%, 80%, 90%, or 100% of the layer or substrate upon which is rests.

A biosensor of the invention can disposable. In one embodiment of the invention, a biosensor is stable at room temperature (about 20 to 22° C.), field temperatures (about 0 to 49° C.), refrigeration temperature (about 1 to 5° C.), or freezing temperature (about 0 to −70° C.) for about 1 day, 2 days, 3 days, 4 days, 5 days, 1 week, 2 weeks, 3 weeks, 4 weeks, 2 months, 3 months, 6 months, 1 year, 2 years or longer. Each individual biosensor can be disposable after one use or can be stripped of analyte and used again.

Graphene Nanoplatelets, Fullerenes, and Carbon Nanotubes

Graphene nanoplatelets can have an average thickness of about 4, 5, 6, 7, 8, 9, 10, or more nanometers up to 50 microns. Graphene nanoplatelets are comprised of short stacks of platelet-shaped graphene sheets that are identical to those found in the walls of carbon nanotubes, but in a planar form. Hydrogen or covalent bonding capability can be added through functionalization at sites on the edges of the platelets. Enhanced properties, such as barrier properties and improved mechanical properties (stiffness, strength, and surface hardness) can be achieved with graphene nanoplatelets due to their unique size and morphology. Graphene nanoplatelets can have a bulk density of about 0.03 to about 0.1 g/cc, an oxygen content of about 99.5 wt %, and a residual acid content of about 98 wt %.

A graphene nanoplatelet biosensor layer can be about 0.1, 0.5, 1, 1.5, 2, 3, 4, 5, or more nm thick (or any range between about 0.1 and 5 nm thick).

Fullerenes can be used as a layer of a biosensor. Buckminsterfullerene ($C_{60}$) has a truncated icosahedron structure with 60 vertices and 32 faces (20 hexagons and 12 pentagons where no pentagons share a vertex) with a carbon atom at the vertices of each polygon and a bond along each polygon edge. A $C_{60}$ molecule is extremely stable, and is able to withstand high temperatures and high pressures. The exposed surface of the structure can selectively react with other species while maintaining the spherical geometry. Atoms and small molecules can be trapped within the molecule without reacting. Other fullerenes include, for example, $C_{20}$, $C_{72}$, $C_{76}$, $C_{78}$, $C_{80}$, $C_{84}$, $C_{100}$, and carbon nanobuds.

The fullerene biosensor layer can be about 0.01, 0.1, 0.5, 1.0, 5.0, 10.0 nm thick (or any range between about 0.01 nm and 10.0 nm).

Carbon nanotubes can be used as a layer of the biosensor. Carbon nanotubes are seamless cylindrical hollow fibers, comprised of a sheet of pure graphite (a hexagonal lattice of carbon), having a diameter of about 0.7 to about 50 nanometers with lengths generally in the range of 10's of microns. Carbon nanotubes can have a length-to-diameter ratio of up to 132000,000:1. The carbon nanotubes can be single-wall nanotubes or multiple-wall nanotubes.

A carbon nanotube biosensor layer can be about 0.01, 0.1, 0.5, 1.0, 5.0, 10.0 nm thick (or any range between about 0.01 nm and 10.0 nm)

Polymers

A polymer for use in a biosensor of the invention should be selected such that it optimizes the non-covalent π-π stacking interaction between the graphene platelets, fullerene, or carbon nanotubes and polymer. Polymers of the invention can include, for example, amphiphilic block copolymers. In one embodiment of the invention, polymers of the invention comprise an aromatic hydrophobic polymer block.

An amphiphilic block copolymer can comprise at least one block of hydrophobic polymers with aromaticity. These hydrophobic aromatic blocks of amphiphilic diblock copolymers can comprise polystyrene, polyquinoline, polynaphthalene, poly(ethylene therephthalate), polyxylene, polytoluene, polydiphenylmethane, polypropylbenzene, polythiophene, polyfluorene, polyphenylene, polypyrene, polyazulene, polyacetylene, polysulfone, polyethersulfone, polyphenylene ether polyphenylene oxide, polycarbonate, poly(phthalazinone ether sulfone ketone), polyether ketone, polyether ether ketone, polyether ketone ketone, polyimide, polyetherimide, and polyamide-imide, and similar.

Amphiphilic block copolymers may comprise two, three, four, five, or more blocks. For example, the amphiphilic block copolymer may be of the general formula A-B, B-A, A-B-A, B-A-B, A-B-A-B-A, or B-A-B-A-B, wherein A represents a hydrophilic block and B represents a hydrophobic block. Amphiphilic block copolymers can be in a linear formation or a branched, hyper-branched, dendrimer, graft, or star formation (e.g., A(B)n, (AB)n, AnBm starblocks, etc.). Amphiphilic block copolymers can comprise hydrophilic blocks at the termini. Blocks of the amphiphilic block copolymers can be of variable length. Blocks of amphiphilic block copolymers can comprise from about 2 to about 800 repeating units, from about 5 to about 200, from about 5 to about 150, or from about 5 to about 100 repeating units.

Blocks of the amphiphilic block copolymer can comprise a single repeating unit. Alternatively, the blocks can comprise combinations of different hydrophilic or hydrophobic units.

Examples of amphiphilic block copolymers include, without limitation: poly(2-oxazoline) amphiphilic block copolymers, polyethylene glycol-polylactic acid (PEG-PLA), PEG-PLA-PEG, polyethylene glycol-poly(lactic-co-glycolic acid) (PEG-PLGA), polyethylene glycol-polycaprolactone (PEG-PCL), polyethylene glycol-polyaspartate (PEG-PAsp), polyethylene glycol-poly(glutarnic acid) (PEG-PGlu), polyethylene glycol-poly(acrylic acid) (PEG-FAA), polyethylene glycol-poly(methacrylic acid) (PEG-PMA), polyethylene glycol-poly(ethyleneimine) (PEG-PEI), polyethylene glycol-poly(L-lysine) (PEG-PLys), polyethylene glycol-poly(2-(N,N-dimethylamino)ethyl methacrylate) (PEG-PDMAEMA), polyethylene glycol-chitosan, and derivatives thereof. Examples of other biocompatible amphiphilic compounds include phospholipids and PEGylated phospholipids.

Examples of hydrophilic blocks include, without limitation, polyetherglycols, dextran, gelatin, albumin, poly(ethylene oxide), methoxy-poly(ethylene glycol), copolymers of ethylene oxide and propylene oxide, polysaccharides, polyvinyl alcohol, polyvinyl pyrrolidone, polyvinyltriazole, N-oxide of polyvinylpyridine, N-(2-hydroxypropyl)methacrylamide (HPMA), polyortho esters, polyglycerols, polyacrylamide, polyoxazolines (e.g., methyl or ethyl poly(2-oxazolines)), polyacroylmorpholine, and copolymers or derivatives thereof. Examples of hydrophobic blocks include, without limitation, polyanhydride, polyester, poly (propylene oxide), poly(lactic acid), poly(lactic-co-glycolic acid), poly(lactic-co-glycolide), poly aspartic acid, polyoxazolines (e.g., butyl, propyl, pentyl, nonyl, or phenyl poly (2-oxazolines)), poly glutamic acid, polycaprolactone, poly (propylene oxide), poly(1,2-butylene oxide), poly (n-butylene oxide), poly(ethyleneimine), poly (tetrahydrofurane), ethyl cellulose, polydipyrolle/dicabazole, starch, and/or poly(styrene).

The hydrophilic blocks of amphiphilic block copolymers can comprise poly(ethylene oxide) (i.e., polyethylene glycol), poly(acrylic acid). Hydrophobic blocks of amphiphilic block copolymers can comprise polyanhydride, polyester, poly(lactic acid), polycaprolactone, poly(propylene oxide), poly(1,2-butylene oxide), poly (n-butylene oxide), poly(tetrahydrofuran), and/or poly(styrene).

An amphiphilic block copolymer can comprise at least one block of poly(oxyethylene) and at least one block of poly(oxypropylene). An amphiphilic block copolymer is a triblock of poly(oxyethylene)-poly(oxypropylene)-poly (oxyethylene).

Polymers comprising at least one block of poly(oxyethylene) and at least one block of poly(oxypropylene) include lipoloxamers, PLURONIC™, poloxamers, and synperonics. Examples of poloxamers include, without limitation, PLURONIC™ polymers include, for example, L31, L35, F38, L42, L43, L44, L61, L62, L63, L64, P65, F68, L72, P75, F77, L81, P84, P85, F87, F88, L92, F98, L101, P103, P104, P105, F108, L121, L122, L123, F127, 10R5, 10R8, 12R3, 17R1, 17R2, 17R4, 17R8, 22R4, 25R1, 25R2, 25R4, 25R5, 25R8, 31R1, 31R2, and 31R4.

Polymers of the invention can include, for example, polystyrene diblock copolymers including, for example, Poly(styrene-block-methyl methacrylate), Poly(styrene)-block-poly(acrylic acid), Polystyrene-block-poly(tert-butyl acrylate), Poly(styrene)-block-poly(ethylene glycol), poly (styrene-B-acrylamide), poly(styrene-B-acrylic acid), poly (styrene-B-cesium acrylate), poly(styrene-B-ethylene oxide), poly(styrene-B-methacrylic acid), poly(4-styrene-sulfonic acid-B-ethylene oxide), poly(styrenesulfonic acid-B-methylbutylene), poly(styrene-B—N,N-dimethylacrylamide), poly(styrene-B—N-isopropyl acrylamide), poly (styrene-B—N-methyl 2-vinyl pyridinium iodide), poly (styrene-b-N-methyl-4-vinyl pyridinium iodide), poly (styrene-b-propylacrylic acid), poly(styrene-b-sodium acrylate), poly(styrene-b-sodium methacrylate), poly(p-chloromethyl styrene-b-acrylamide), poly(styrene-co-p-chloromethyl styrene-b-acrylamide), poly(styrene-co-p-chloromethyl styrene-b-acrylic acid), poly(styrene-b-methylbutylene-co-isoprene sulfonate).

A polymer of a device can be one or more amphiphilic block copolymers such as poly(styrene) block-poly (acrylic acid) (PS-b-PAA).

A polymer biosensor layer of the invention can be about 0.1, 0.5, 1, 2, 3, 4, 5, 6, 7, 8, 9, 10 or more nm thick (or any range between about 0.1 and 10 nm).

Analytes

Biosensors of the invention can be used to detect analytes such as enzymes, antibodies, proteins, peptides, and nucleic acids in a sample. Analytes can be, for example, ascorbic acid, dehydroascorbic acid, glucose, lactate, uric acid, sialic acid, lactic acid, interleukins, TNF-α, small molecules, immunoglobulins (e.g., IgM, IgG, sIgA), lysozyme, bicarbonates, glucose, lactoferrin, lipocalin, and electrolytes ($Na^+$, $K^+$, $Cl^-$, $HCO^-$, $Mg^{2+}$, $Ca^{2+}$), lipids (meibomian glands), defensins, collectins, cortisol and dehydroepiandrosterone (DHEA), serotonin, cytokines, inflammatory mediators, growth factors, white blood cells, antigens, signaling molecules, complement components, remodeling enzymes, lypocalin, mucins (epithelial membrane-anchored type, soluble goblet-cell type), or albumin, b-FGF.

In one embodiment an analyte is present in a biological sample such as be tears, tear film, aqueous layer of the tear film, aqueous humor, sweat, blood, serum, plasma, urine, saliva, or other bodily fluids.

An analyte can be present in tear film or aqueous humor. In one embodiment, an analyte is present in both the aqueous humor and in the tear film, but in a normal, non-diseased or non-injured subject is present in the aqueous humor at a higher concentration than in the tear film. In another embodiment, the analyte is present in the aqueous humor and is not present in the tear film in a normal, non-diseased, non-injured subject. When an eye condition is present, the amount of analyte increases in the tear film due to leakage or movement from the aqueous humor to the tear film.

Analyte Ligands

A ligand is a substance that forms a complex with an analyte through, for example, ionic bonds, hydrogen bonds, Van der Waals forces, covalent bonds, non-covalent bonds, electrostatic interactions, π-effects, or hydrophobic effects.

The interaction of ligands with their analytes can be characterized in terms of a binding affinity. For example, a ligand can bind an analyte with a $K_d$ equal to or less than about $10^{-7}$ M, such as but not limited to, $0.1\text{-}9.9 \times 10^{-3}$, $10^{-4}$, $10^{-5}$, $10^{-6}$, $10^{-7}$, $10^{-8}$, $10^{-9}$, $10^{-10}$, $10^{-11}$, $10^{-12}$, $10^{-13}$, $10^{-14}$, $10^{-15}$ or any range or value therein. A ligand can bind an analyte with an off rate ($K_{off}$) of less than or equal to $0.1\text{-}9.9 \times 10^{-3}$ $sec^{-1}$, $10^{-4}$ $sec^{-1}$, $10^{-5}$ $sec^{-1}$, $10^{-6}$ $sec^{-1}$, $10^{-7}$ $sec^{-1}$. A ligand can bind an analyte with an on rate ($K_{on}$) greater than or equal to $0.1\text{-}9.9 \times 10^3$ $M^{-1}$ $sec^{-1}$, $10^4$ $M^{-1}sec^{-1}$, $10^5$ $M^{-1}$ $sec^{-1}$, $10^6$ $M^{-1}sec^1$, $10^7$ $M^{-1}sec^{-1}$, $10^8$ $M^{-1}sec^{-1}$.

A ligand for an analyte can be, for example, an antibody (or specific binding portion thereof) that specifically binds the analyte, an antibody fraction, a nucleic acid, a protein, a peptide, a peptidomimmetics, an ion, a small molecule, an enzyme, an aptamer.

A ligand for ascorbic acid can be, for example, ascorbate oxidase, or an antibody that specifically binds ascorbic acid. A ligand for AA can also be a dual molecule comprised of a fluorescent chromophore and a nitroxide radical (the nitroxide acts as a quencher of the fluorescence of the chromophore fragment). The reduction of the nitroxide fragment by ascorbic acid results in decay of ESR (electron spin resonance) signal and enhancement of the fluorescence.

The ligand for the analyte can be an enzyme. In one embodiment of the invention, the enzyme is ascorbate oxidase, which can be present in a biosensor of the invention at a concentration at about 3, 5, 10, 12, 15, 20, 30, 40, 50, 60, 70, 80, 90, 100 or more U/cm$^2$.

Examples of ligands include for example: sythetic lectins for glucose (Ke et al., Nature Chemistry, D01:10.1038 NCHEM.1409); 5-amino-2-hydroxymethylphenyl boronic acid for lactate; polymers for uric acid (US Publ. 20030039627); lectins for sialic acid (Zeng & Gabius, Z. Naturaforsch. C. (1992) 47:641); trivalent chromium and dextran for lactic acid; antibodies, interleukin receptors, or binding portions thereof for interleukins; antibodies, TNF-α receptors, or binding portions thereof for TNF-α; antigens for immunoglobulins (e.g., IgM, IgG, sIgA); anti-σ factor RsiV and dapsone for lysozyme; carbonic anhydrase and phosphoenolpyruvate carboxylase for bicarbonate; Pneumococcal surface protein A, GAPDH, osteopontin, and DNA for lactoferrin; enterobactin for lipocalin; heparin, Na$^+$/K$^+$ ATPase, glycine, polystrene sulfonate resin, valinomycin, aequorin, chromomycin3, norfloracin, cholera toxin, troponinC, S100A1 binding protein and calsequestrin for electrolytes (Na$^+$, K$^+$, Cl$^-$, HCO$^-$, Mg$^{2+}$, Ca$^{2+}$); Staphylokinase and heparin for defensins; Gp340 and calreticulin for collectins; corticosteroid binding globulin for cortisol; MAP2 for dehydroepiandrosterone (DHEA); seronectin for serotonin; cytokine receptor proteins or binding portions thereof for cytokines, GroEL, GAPDH from *Mycoplasma genitalium*, LL-37 peptide for mucins; FcRn, Protein G, and albondin for albumin; syndecan, PG-M-CSF, and perlecan for b-FGF. Additionally, ligands in the form of antibodies and specific binding portions thereof are well know to those of skill in the art for the above-mentioned analytes.

In one embodiment of the invention, the ligand for the analyte is stable at room temperature (about 20 to 22° C.), field temperatures (about 0 to 49° C.), refrigeration temperature (about 1 to 5° C.), or freezing temperature (about 0 to −70° C.) for 1 day, 2 days, 3 days, 4 days, 5 days, 1 week, 2 weeks, 3 weeks, 4 weeks, 2 months, 3 months, 6 months, 1 year, 2 years or longer.

Substrate

In one embodiment of the invention, the biosensor is supported by a substrate. The substrate can comprise one or more of an acrylamide, cellulose, nitrocellulose, glass, indium tin oxide, silicon wafer, mica, polystyrene, or polyvinylidene fluoride (PVDF) filter, filter paper (e.g., VVhatman), glass fiber filters (GF), fiberglass, polyethylimine coated GFs, porous mylar or other transparent porous films, cellulose nitrate (CN) membrane, mixed cellulose ester membrane, cellulose acetate membrane, polyethersulfone (PES) membrane, PTFE membrane, ultrafiltration membranes of poly(vinyl chloride) (PVC), carboxylated poly (vinyl chloride) (CPVC), polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfumarate, collagen, glycosaminoglycans, and polyamine acids. The substrate can be formed into pre-perforated strips, individual strips, individual sheets, or any other suitable shape.

Electrode

An electrode is a composition that, when connected to an electronic device, is able to sense a current or charge and convert it to a signal. Alternatively, an electrode can be a composition that can apply a potential to and/or pass electrons to or from connected devices.

Electrodes include, but are not limited to, certain metals and their oxides, including gold; copper; platinum; palladium; silicon; aluminum; metal oxide electrodes including platinum oxide, titanium oxide, tin oxide, indium tin oxide, palladium oxide, silicon oxide, aluminum oxide, molybdenum oxide (Mo$_2$O$_6$), tungsten oxide (WO$_3$) and ruthenium oxides; and carbon (including glassy carbon electrodes, graphite and carbon paste). In one embodiment, the electrode can be an interdigitated electrode, micro-interdigitated gold electrode (MICE), or a digitated electrode (e.g., a digitated gold electrode).

In one embodiment of the invention, gold is deposited on a biosensor electrode at a thickness of about 50, 100, 200, 300, 400, 500, or more nm.

The electrode can be a planar electrode. The electrode can be deposited on a biosensor by a variety methods including, but not limited to, screen-printing or evaporation. An electrode may be open or covered by a cover to form a defined volume cell.

A biosensor electrode can detect a change in resistance caused by the interaction of a ligand and an analyte such as ascorbate oxidase. The change in resistance can indicate an amount of analyte present in the sample.

Fluidic Chamber

A biosensor of the invention can comprise a fluidic chamber such as a microfluidic chamber. The fluidic chamber can accommodate a fluid volume of about 0.1, 0.5, 1.0, 5, 10, 15, 20, 50, 100 μL or more (or any range between about 0.1 and 100 μL). The fluidic chamber can be made of polyester or any other suitable material. A fluidic chamber can be present in a biosensor of the invention such that a test sample is delivered to and held in contact with the biosensor. For example, the microfluidic chamber can accept a sample and guide the sample to the top of the analyte ligand layer, to the electrode, or to the top of the polymer layer. A fluidic chamber can comprise a layer on top of the analyte ligand layer.

Cover

A biosensor can comprise a cover comprised of plastic or other suitable material. The cover can protect the fluidic chamber, the analyte ligand layer, the electrode, the polymer layer, or combinations thereof. A cover can be present on top of a fluidic chamber, an analyte ligand layer, an electrode or a polymer layer.

Embodiments without an Electrode

In some embodiments, an electrode is not used for detection of analyte/ligand binding or interaction. Instead other methods can be used to detect binding. In these embodiments an electrode can be absent from the biosensor structure. For example, the increased amount of mass on the biosensor when a ligand binds or interacts with an analyte in a sample can be detected. Additionally, a colorimetric or fluorescent change that occurs when a ligand binds an analyte can be detected. A change in a Raman spectroscopy or Fourier transform infrared spectroscopy reading can also be used to detect analyte/ligand binding or association. In other embodiments, electrochemical changes can be detected, fluorometric changes can be detected with HPLC, and immunoassay changes can be detected by HPLC. Gas chromatographic detection with mass spectrometry (GC-MS) can also be used to detect ligand/analyte binding.

Devices

The invention also provides a device comprising a biosensor and a detector. The detector can be connected to a data acquisition system.

The detector can comprise a digital or analog multimeter that can measure voltage, current, and resistance. A detector can also be a spectrophotometer, fluorometer, or a spectrometer like a Raman spectrometer or a Fourier transform infrared spectrometer.

The data acquisition system can be selected from the group consisting of a computer, a hand-held device, a cell phone, and a tablet. The detector provides information (e.g., a sample identifier, a subject identifier, a quantity detected of one or more analytes, a positive or negative reading regarding the presence or absence of an analyte, or a combination thereof) to the data acquisition system, which can then analyze the information and provide an easy to read and interpret result.

A device can further comprise a screen that allows for visualization of an amount of an analyte, such as ascorbic acid, present in a sample.

A device can be battery operated.

The invention provides kits comprising one or more biosensors, one or more disposable biosensors, a detector, a data acquisition system, or combinations thereof.

Methods of Detection of Analytes and Diagnosis

The invention provides methods for detecting an eye condition in a subject comprising detecting the level or amount of ascorbic acid in a tear film sample from a subject. An elevated level of ascorbic acid indicates an eye condition is present in the subject. The level or amount of ascorbic acid in a tear film can be compared to a control sample or control standard. If an elevated level of ascorbic acid is present in the tear film, then a medical practitioner can administer one or more treatments (e.g., surgery, administration of medication, etc.) to the subject. The level or amount of ascorbic acid can be measured or detected by any method known in the art including, for example, the biosensors of the invention. Other detection methods include absorbance assays, colorimetric assays, fluorescent assays, and spectroscopy such as Raman spectroscopy or Fourier transform infrared spectroscopy.

The invention also provides methods of detecting an analyte such as ascorbic acid in a sample comprising contacting a biosensor of the invention with the sample and detecting the analyte with a detector.

The detector can detect binding of the analyte and the analyte ligand due to a change in electrical resistance caused by interaction of the analyte in the sample with the analyte ligand; due to a change in mass on the biosensor; due to a colorimetric change; due to a fluorescent reaction; due to a change in a Raman spectroscopy reading, or due to a change in a Fourier transform infrared spectroscopy reading. In one embodiment, after contacting a biosensor with a sample, the biosensor is inserted into or onto a device comprising a detector to measure a change caused by interaction of an analyte in the sample and a ligand for the analyte such as a change in electrical resistance. A screen for visualizing the change in resistance is provided such that an analyte in the sample is detected.

The presence, absence, or an amount of an analyte in the sample can be detected. The amount of an analyte, such as ascorbic acid, can indicate the severity of the eye condition. That is, the higher the amount of analyte, e.g., ascorbic acid, the greater the severity of the disease or condition (e.g., an eye condition).

The invention provides methods of diagnosing an eye condition. The method comprises contacting a biosensor with a tear; tear film; aqueous layer of the tear film, or aqueous humor sample of a subject and detecting an amount of an analyte in the sample. An eye condition is diagnosed in the subject where the concentration of the analyte in the sample is elevated as compared to a control sample or control standard. The eye condition can be selected from a full or partial thickness laceration or perforation to the anterior chamber of the eye, eye disease, mechanical or chemical eye injury, anterior scleral injury, corneal wound integrity, aqueous humor leaks, eye ulcer; infection, or surgical incisions.

Methods and compositions of the invention can provide specificity (ability of an assay to measure a specific analyte, e.g., ascorbic acid, rather than other analytes in a sample. The specificity can be, for example, 70, 75, 80, 90, 95, 96, 97, 98; 99% or more. Methods and compositions of the invention can provide 10, 9, 8; 7, 6, 5, 4, 3, 2, 1% or less false positive results.

In one embodiment of the invention, a biosensor of the invention can be used to detect an analytes such as ascorbic acid in other types of samples such as sweat, blood, serum, plasma, urine, saliva, or other bodily fluids to diagnose or detect other conditions.

Analytes such as ascorbic acid can be found in higher amounts or levels in injured or diseased samples (e.g., a sample of a subject with an eye condition) as compared to control subject samples from non-injured or non-diseased subjects. The relative levels of analytes, such as ascorbic acid, in subject samples can indicate progression of disease and disease severity. That is, in some instances, a greater amount or level of analyte in a test sample means a more severe disease state or condition.

Elevated levels of analytes, such as ascorbic acid, are levels that are about 10, 20; 30, 40, 50; 60, 70, 80; 90, 100; 200, 300; 400, 500% or more than control samples or control standards. Elevated levels of analytes such as ascorbic acid are levels that are about 10 to 500% more; about 20 to 500% more; about 30 to 500% more; about 40 to 500% more; about 50 to 500% more; about 60 to 500% more; or about 100 to 500% more than control samples or control standards.

Elevated levels of analytes such as ascorbic acid can also be levels that are statistically significantly increased amounts when compared to control samples or control standards.

Elevated levels of ascorbic acid can also be about 40, 50, 60, 70, 80, 90, 100, 200, 300, 400, 500, 600, 700, 800, 900, 1,000, 1,100, 1,200, 1,300, 1,400 or more micromol/L (or any range between about 40 and about 1,400 micromol/L, for example about 50 to about 1,400; between about 100 and about 1,400, between about 500 and about 1,400 micromol/L). Control levels or control standards of ascorbic acid can be about 50, 40, 30, 20, 10 or less micromol/L (or any range between about 10 and about 50, between about 10 and about 40, between about 10 and 30, or between about 10 and 20 micromol/L).

Elevated levels of analytes such as ascorbic acid can be compared to control samples or control standards that are determined using normal control subjects who do not have any type of disease, eye disease, or eye condition.

In some embodiments, the level of analytes such as ascorbic acid in a test sample is compared the level of the analyte in a control sample from one or more normal control subjects. Typically, the measured control level in the control sample is then compared with the analyte level measured in the test sample. Alternatively, the level of an analyte such as ascorbic acid in the test sample is compared to a previously determined or predefined control level (a "control standard"). For example, the control standard for an analyte such as ascorbic acid of can be calculated from data, such as data including the levels of the analyte in control samples from a plurality of normal control subjects. The normal control subjects and the test subject under assessment can be of the same species.

As used herein, "patient" or "subject" means an individual having symptoms of, or at risk for, eye disease, eye condition, or eye injury, or other disease, condition, or malignancy. A patient may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human such as canine, feline, bovine, equine, or rodent) that may benefit from the methods and compositions contemplated herein.

Results (i.e., the presence; absence; or amount of an analyte) can be delivered with about 10, 5, 4, 3, 2, 1 minute or less using only small sample sizes (e.g., about 50, 20, 15, 10, 5, 2, 1.0, 0.5 or less µL).

Unless otherwise explained, all technical and scientific terms used herein have the same meaning as commonly understood by one of ordinary skill in the art to which a disclosed disclosure belongs. The singular terms "a," "an," and "the" include plural referents unless context clearly indicates otherwise. Similarly, the word "or" is intended to include "and" unless the context clearly indicates otherwise. "Comprising" means "including"; hence, "comprising A or B" means "including A" or "including B" or "including A and B."

While the present disclosure can take many different forms, for the purpose of promoting an understanding of the principles of the disclosure; reference will now be made to the embodiments illustrated in the drawings and specific language will be used to describe the same. It will nevertheless be understood that no limitation of the scope of the disclosure is thereby intended. Any alterations and further modifications of the described embodiments, and any further applications of the principles of the disclosure as described herein are contemplated as would normally occur to one skilled in the art to which the disclosure relates.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof; but it is recognized that various modifications are possible within the scope of the disclosure. Thus, it should be understood that although the present disclosure has been specifically disclosed by preferred embodiments, exemplary embodiments and optional features, modification and variation of the concepts herein disclosed may be resorted to by those skilled in the art, and that such modifications and variations are considered to be within the scope of this disclosure as defined by the appended aspects. The specific embodiments provided herein are examples of useful embodiments of the present disclosure and it will be apparent to one skilled in the art that the present disclosure may be carried out using a large number of variations of the devices, device components, methods steps set forth in the present description. As will be obvious to one of skill in the art, methods and devices useful for the present methods can include a large number of optional composition and processing elements and steps.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the aspects herein.

EXAMPLES

Example 1

GR-Polymer Composites for Preparation of Conductive Filter Paper

Graphene is a zero-overlap semimetal with both holes and electrons as charge carriers infers very high electrical conductivity. In graphene, 3 other carbon atoms connected to each carbon in two dimensional plane, while 1 electron ($\pi$) freely available in the third dimension, above and below the graphene sheet for electronic conduction. The electronic properties of graphene are dictated by the valance and conduction bands (bonding and anti-bonding) of these pi orbitals.

Dirac points in graphene (electrons and holes) have zero effective mass and the energy-movement relation (the spectrum for excitations) is linear for low energies near the 6 individual corners of the Brillouin zone. At the Dirac points, electronic conductivity is actually quite low due to the zero density of states. But the doping with electrons or holes, the Fermi level can be changed to create a material that is potentially better at conducting electricity.

The electronic mobility of graphene is very high: above 15,000 $cm^2 \cdot V^{-1} \cdot s^{-1}$ with theoretically potential limits of 200,000 $cm^2 \cdot V^{-1} \cdot s^{-1}$ (limited by the scattering of graphene's acoustic photons). These charge carriers are able to travel sub-micrometer distances without scattering; a phenomenon known as ballistic transport. However, the quality of the graphene and the substrate that is used is important. With silicon dioxide as the substrate, for example, mobility is potentially limited to 40,000 $cm^2 \cdot V^{-1} \cdot s^{-1}$.

Fabrication Methods of a Biosensor

In order to measure ascorbic acid (AA) in bio-fluids sample collected from, e.g. eye, an electrical-based biosensor was designed. So as to reduce the cost of biosensor and making it a field-deployable point of care biosensor device, filter paper was chosen as a biosensor substrate. The specificity of the biosensor to detect ascorbic acid is achieved by coating the substrate with ascorbate oxidase on top of multiple layers of Poly(styrene)-block-poly(acrylic acid) (PS-b-PAA) and graphene platelets. Here, PS-b-PAA acts as a binder and graphene platelets act as a supporting platform for holding the ascorbate oxidase. The ascorbate oxidase layer was carefully conjugated on top of the graphene platelets layer to expose it for binding events with the ascorbic acid molecules. In order to measure the changes in the surface resistance of graphene layers due to binding of ascorbic acid with the oxidase, about 200 nm of gold were deposited on the top of the biosensors as interdigitated electrodes format.

Change in Resistance Due to Ascorbate Oxidase and Ascorbic Acid on Graphene Platelet Platform.

Optimization of the biosensor lead to two different designs. In one of the designs, a low concentration of graphene platelets was used (FIG. 3a). The other design used a high concentration of graphene platelets (FIG. 3b). Below the percolation threshold, the graphene platelets form a largely unconnected system leading to high surface resistance (>6 MΩ) as shown in FIG. 3a. When the concentration of graphene platelet reaches beyond the percolation threshold, it forms a connected system (FIG. 3b) leading to lower surface resistance (<0.2 MΩ). As we will show later, these two systems lead to two different behaviors for graphene platelet-ascorbic oxidase assembly and with subsequent interaction of ascorbic acid. For example, the system shown in FIG. 3a leads to decrease of surface resistance due to presence of ionic solutions like ascorbic acid (due to formation of conductive channels between graphene platelet islands). On the other hand, system shown in FIG. 3b leads to increase of surface resistance due to product formation of catalysed reaction between ascorbate oxidase and ascorbic acid.

Ascorbic Acid Detection Process

A calibration curve was first generated by measuring the change of resistance of the biosensor with known concentration of ascorbic acid standard solution. The change in resistance was measured using a multi-meter and recorded in a connected laptop. In order to measure the concentration of AA in an unknown sample, the measured resistance corresponding to the sample are compared to that of the calibration curve. The validation of results for unknown samples (e.g. clinical samples) is performed by obtaining the concentration through standard colorimetric assay and mass spectrometric based analytical methods.

Layer by Layer Assembly of the Biosensor and Characterization by Raman Spectroscopy A biosensor was formed by first immobilizing several layers of graphene platelets on a filter paper substrate. The Raman spectrum of D, G and 2D peaks are clearly visible in FIG. 4 (top curve). Since, with the subsequent polymer layer on the graphene platelet, the π-π interaction between graphene-polymer layers will be manifested. Thus, more energy will be required to vibrate the bonds and difficult to polarize the system. Therefore, the overall intensity decreases (bottom curve) after the formation of polymer layer.

Figure 5:
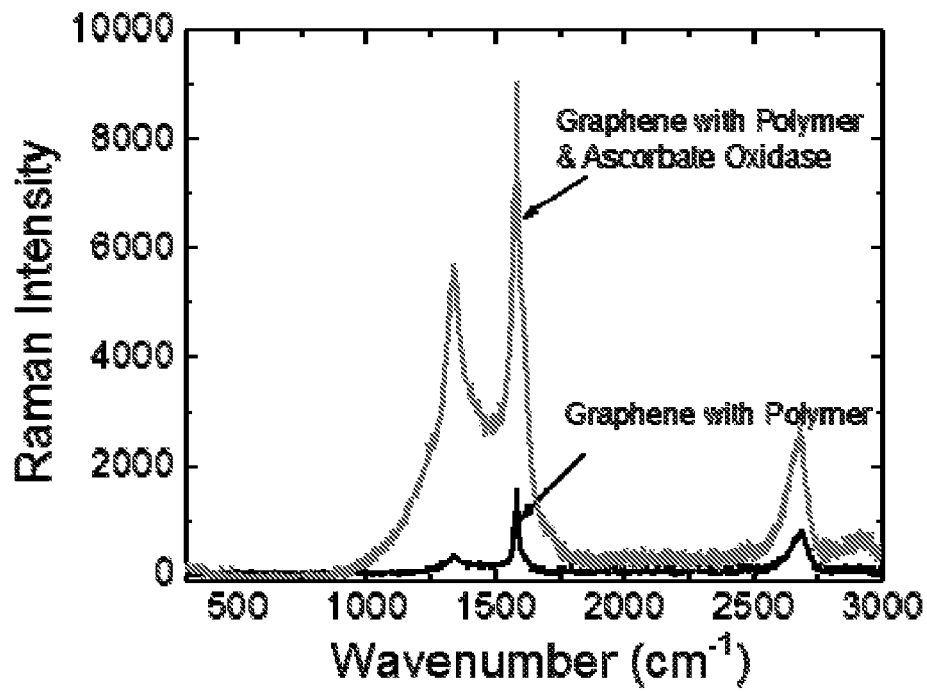
FIG. 5. Raman spectra showing the graphene platelet with polymer layer and the subsequent ascorbate oxidase layer.

Wth the subsequent layering of ascorbate oxidase on top of the polymer layer (of Poly(styrene)-block-poly(acrylic acid), the interplay between π-π interaction between graphene-polymer and polymer-oxidase comes in to picture. The polymer-oxidase interaction lessens the effect of graphene-polymer interaction and hence the overall intensity rises (top curve) compared to without the oxidase layer (bottom curve) as shown in FIG. 5.

Figure 6:
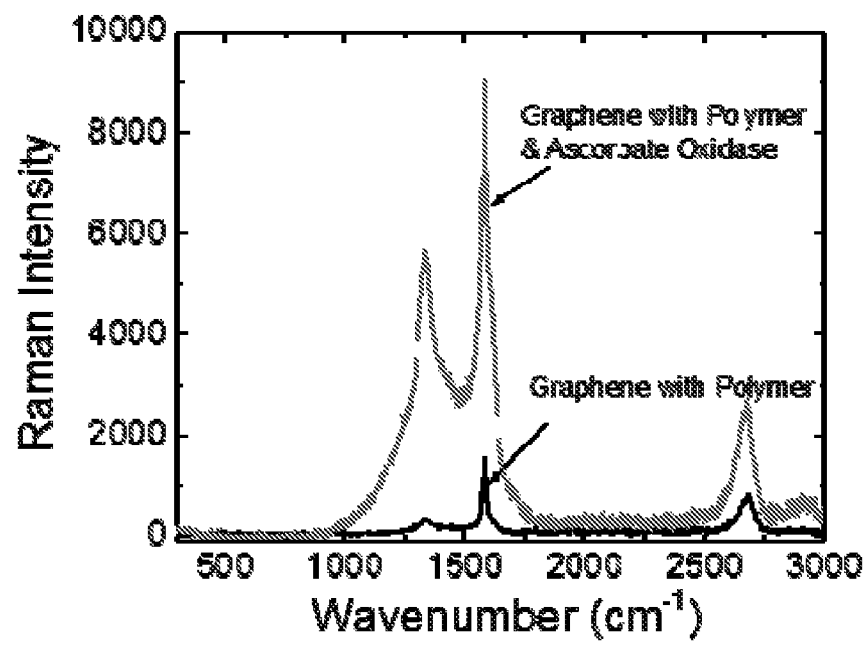
FIG. 6. Raman spectra showing the graphene platelet with polymer layer and ascorbate oxidase layer with or without ascorbic acid.
Figure 7:
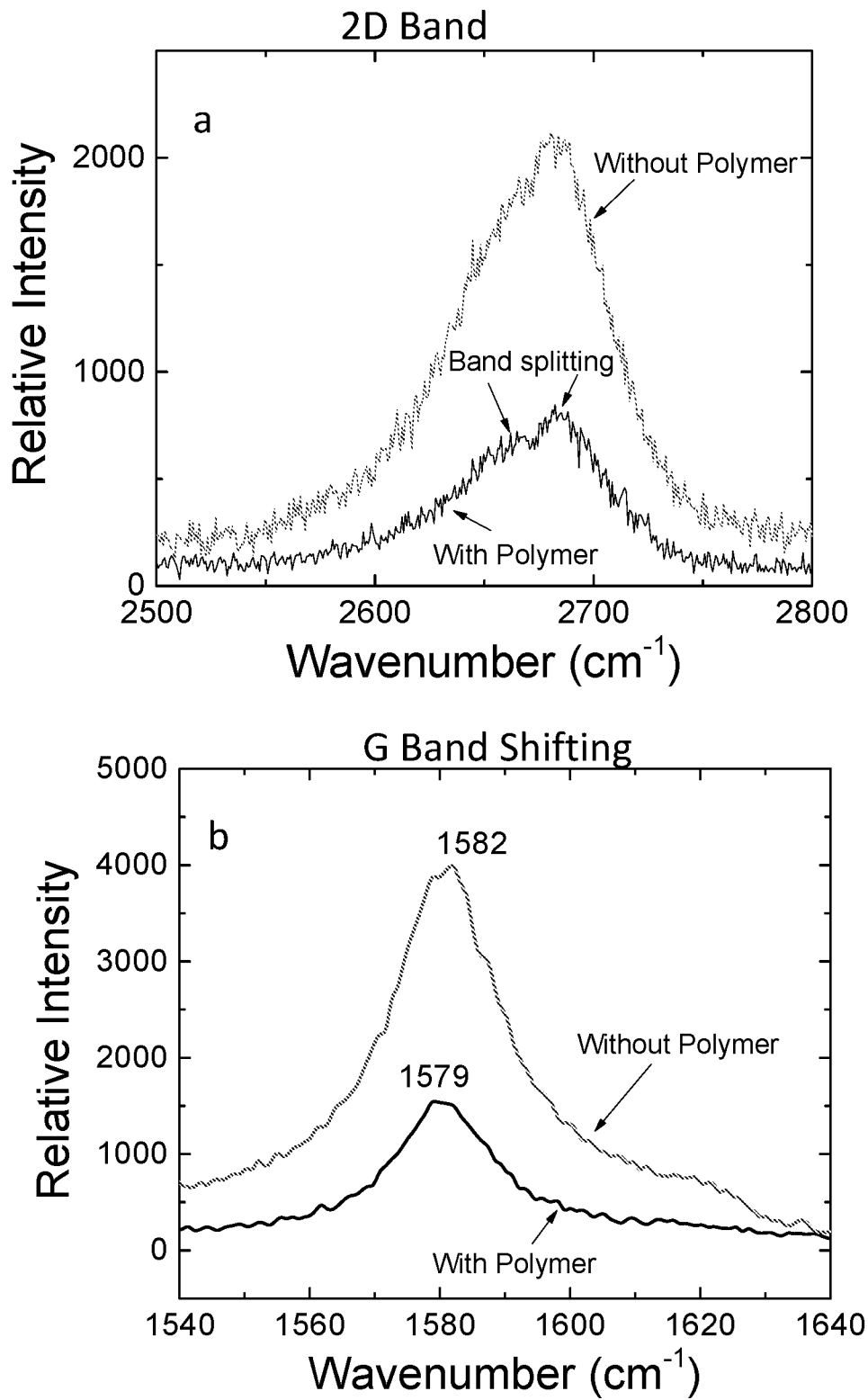
FIG. 7. Raman spectra showing the 2D band splitting (a) as an indication of layer stacking, and (b) while as the number of layer on graphene increases the G band position shifts to lower frequency.

FIG. 6 shows the result due to interaction between polymer-oxidase and oxidase-ascorbic acid. The graphene-polymer interaction increases due to oxidase-ascorbic acid strong interaction. This leads to overall intensity decrease (top curve) after dropping ascorbic acid on the biosensor.

Ascorbic Acid Concentrations in Clinical Samples as Compared with Standards

A total of 16 clinical samples were tested to determine the concentration of ascorbic acid. For the testing of clinical samples, the biosensors were tested to have initial resistance below 2MΩ (Type-II). As expected the resistance increased with clinical sample confirming the presence of ascorbic acid. Using the calibration curve, the predicted ascorbic acid concentrations are reported in Table 1.

TABLE 1

Concentration of ascorbic acid measured using Biosensor

| Clinical Sample Identification Number | Predicted Ascorbic Acid Concentration (μM) |
|---|---|
| 1 | 1000 |
| 2 | 2375.0 |
| 3 | 2035.0 |
| 4 | <50 |
| 5 | ND |
| 6 | 429.0 |
| 7 | 283.0 |
| 8 | 565.5 |
| 9 | <50 |
| 10 | <50 |
| 11 | <50 |
| 12 | 586.0 |
| 13 | 2000 |
| 14 | 1696.0 |
| 15 | <50 |
| 16 | <50 |

Example 2

A point-of-service biosensor device to measure AA concentration in the human ocular tear film that can be translated to clinical use for evaluation of the anterior of anterior ocular wounds was developed. A power analysis suggested that 15 samples would be needed to achieve <5% standard error of mean (SEM) for the biosensor compared to colorimetric test. The aqueous humor AA concentration of 23 μM and standard deviation (SD) of 9.6 μM for healthy individuals is considered for the calculation. Samples of aqueous humor were collected and sent to the research laboratory for testing. The samples were collected from patients with localized retinal detachments who were scheduled for therapeutic paracentesis to release intraocular pressure after therapeutic pneumatic retinopexy as standard of care. The fluid was removed in a controlled clinical setting after placement of a topical anesthetic drop of proparacaine and antibiotic drop of ocufloxacin on the cornea of the patient. The fluid was collected using a sterile 30-gauge needle attached to a sterile one-milliliter syringe.

Preparation of GRP-Polymer Composites

Graphene platelet (0.1 mg/mL) was mixed with polystyrene-block-polyacrylic acid (PS-b-PAA) amphiphilic polymer suspension (0.1 mg/mL) in water. Mixture (GRP-polymer) was probe sonicated at amplitude 4, with pulse of 5 sec on and 1 sec off for 4 h with intermittent cycles of 30 min. The process was completed at controlled temperature of 60° C. A suspension of GRP-polymer was stored at 4 in germ free conditions before use for preparing GRP-polymer coated filter paper.

Methodology of Surface Coating on Filter Paper

Whatman filter paper of diameter 7 cm was used to be coated with GRP-polymer composites by dip-dry method. Whatman filter paper was dipped in 10 mL of GRP-polymer suspension and incubated at RT for solvent evaporation under controlled atmosphere and deposition of GRP-polymer composite on filter paper. The procedure was performed under a biosafety hood on sterilized surfaces and germ free environment.

Coating of Ascorbate Oxidase

To make GRP-polymer coated filter papers specifically responsive to AA, AO was surface loaded to GRP-polymer coated filter papers by drop-cast method in BSL2 facility. Each 1 cm$^2$ area of the paper was coated with 12 U of AO which would be enough to interact with 1.2 mg of ascorbic acid specifically. Coated papers were incubated at RT under germ free condition for air drying.

Formation of Interdigitated Electrodes

Interdigitated electrodes were fabricated on a filter paper. In order to make electrodes on filter papers without using lithography process, a shadow mask was fabricated on stainless steel substrate. Uniform layer of gold metal with thickness of ~200 nm were deposited through the shadow mask to fabricate the electrodes using Temescal six pocket E-Beam Evaporation System. After the deposition, individual biosensors were cut and attached with wire bonding process using silver paste to prepare for further experimentation.

Characterization of Biosensor Strips

For atomic force microscopy (AFM) analysis, a square of biosensor strip was attached to AFM disks using double sided carbon tape. AFM images were obtained using an Asylum Cypher (Santa Barbara, Calif., USA) with tapping mode and phase mode. The surface of strip was scanned in air using OMCL-AC160TS cantilevers at a set point of 0.63 V, a 1 Hz scan rate, and a drive frequency of 336.3 kHz.

For TEM, a 50 mm diameter section of a biosensor strip was cut from the whole and placed onto the TEM sample holder. Images were obtained using a Jeol (Peabody, Mass.) 2010 cryo-electron microscope operated at 200 kV, and using different degrees of defocus to obtain an adequate phase contrast. Images were recorded on a Gatan (Pleasanton, Calif.) UltraScan 2 k×2 k CCD.

For X-ray color mapping and SEM imaging, a biosensor square was attached to SEM sample holders using two pieces of copper tape to hold the sample in place. Images obtained using a Hitachi (Schaumburg, Ill.) S-4700 SEM with Oxford Instruments (Abingdon, Oxford shire) ISIS EDS X-ray Microanalysis System and Centaurus BSE detector. The biosensor strip was scanned with an accelerating voltage of 10 kV, extracting current of 10 µA, working distance of 12 mm, in analysis mode. X-ray mapping of 70 compiled scans with 250 µs point dwell time and 512 resolutions.

Specificity of the Biosensor for Ascorbic Acid Using UV-Vis Spectroscopic Studies An aqueous solution of 60 µg (20 U)/mL ascorbate oxidase was studied for absorbance. Further, aliquots (1 µL; Final concentration 50µ) of L-ascorbic acid, L-lactic acid and sialic acid (50 mM) were added sequentially until total concentration reached to 1000 µM. Absorption values acquired after total concentration of L-ascorbic acid, L-lactic acid and sialic acid reached 50, 100, 250, 500, 750 and 1000 were plotted against range of wavelength from 200 to 600 nm. Shifts in $\lambda_{max}$ (x) and absorption efficiency (y) were compared to determine maximum interaction.

Experimental Set-Up for Resistance Measurement

The change in resistance of the graphene platelet-ascorbic oxidase assembly due to presence of different concentration of AA was measured using a digital multimeter connected to a data acquisition system. The data were continuously acquired after dropping the sample on the biosensor until the measurement stabilized (about 3 minutes after the start of recording). The stable resistance value was taken for further analysis to plot calibration curve and measurement of concentration of unknown samples.

Mass Spectrometry

AA was bought from Sigma-Aldrich and was used without purification. LC-HRMS was performed on Waters Synapt G2Si Mass Spectrometry. The column model is ACQUITY UPLC BEH 018; 1.7 µm; 2.1 mm×50 mm. Mobile phase A is 95% $H_2O$, 5% CAN, 0.1% FA, and mobile phase B is 5% $H_2O$, 95% CAN, 0.1% FA. The linear gradient sequence is 100% A, 0% B (0.5 min), 20% A, 80% B (4.0 min). 100% A, 0% B (4.1 min) with the flow rates at 0.3 mL/min. The auto sampler temperature was at room temperature. Negative mass spectrometry and electrospray ionization (ESI) method was used, 2000 V Voltage was used for ion spray, and the source temperature was 400° C.

Results

Design and Fabrication of a Biosensor Prototype

The unique design of the biosensor multilayered test strip utilizes the selective properties of the enzyme ascorbate oxidase (AO) enzyme, which can be placed between graphene platelets and an amphiphilic diblock-copolymer, Poly (styrene)-block-poly(acrylic acid) (PS-b-PAA). Graphene nanoplatelets (STREM CHEMICALS, USA) represent a new class of carbon materials with multifunctional properties having "platelet" morphology. Platelet morphology is defined as having a very thin (~6-8 nm) but wide aspect ratio with width of ~25 µm. This unique morphology makes these particles especially effective at providing barrier properties. In addition, their pure graphitic composition delivers excellent electrical and thermal conducting properties. The paper-based biosensor is made by coating the filter paper (Whatman™; GE healthcare, UK limited; 90 mm qualitative circles) with multiple layers of composite containing Poly (styrene)-block-poly(acrylic acid) (PS-b-PAA) and graphene platelets. The substrate for the biosensor was produced by the sequential deposition of graphene platelet over the filter paper followed by casting a layer of PS-b-PAA. The non-covalent π-π stacking interaction between the two dimensional graphene platelets and multiple repeat units of poly(1-phenylethylene) functionalities of the diblock-copolymer was realized.

Figure 15:
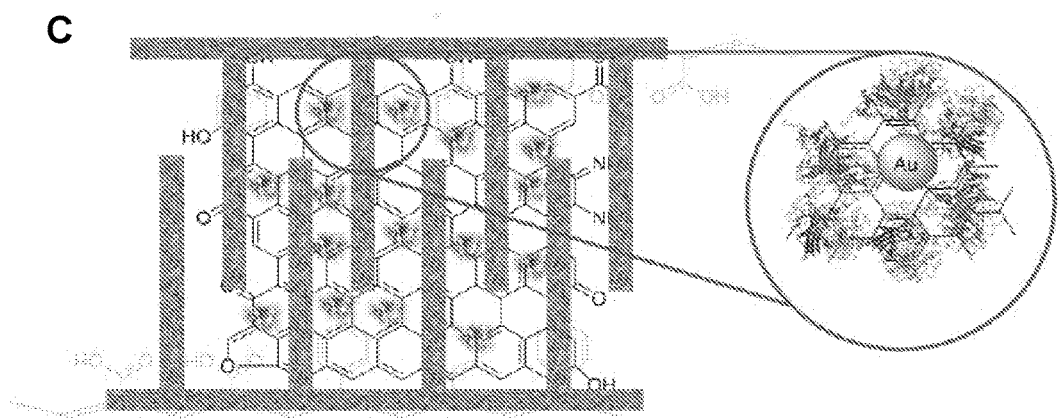
FIG. 15. shows the chemistry of GRP-polymer composites and surface-coated filter paper. (A) PS-b-PAA-Graphene platelet composite; (B) interdigitated gold electrode; (C) ascorbate oxidase (AO) loaded GRP-polymer coated filter paper; (D) ascorbic acid bound AO.

The high specificity of the biosensor to detect AA was achieved by coating AO enzyme on top of the graphene-polymer coating. The acrylic acid (—$CO_2H$) residues of the diblock copolymer were available for facile immobilization of the enzyme over the graphene platelet-polymer composite. The specific interaction of AA with AO produces a difference in the resistance, which can be measured by an impedance-based detector. The disposable biosensor 'strip' was designed to measure the AA in a clinical sample by measuring the change in resistance using a handheld multimeter (FIG. 10A). This reading provides a time sensitive result with the final reading appearing in less than five minutes. The inset of FIG. 10A shows a prototype of the 3D printed model of the handheld biosensor device. The layered architecture and components of a biosensor are schematically shown in FIG. 10B. The AO layer was immobilized on top of the polymer layer to expose it for binding events with the AA molecules (FIG. 15). In order to measure the changes in the surface resistance of graphene layers due to binding of AA with the oxidase, about 200 nm of gold were deposited on the top of the biosensors as interdigitated electrodes format.

Figure 2B:
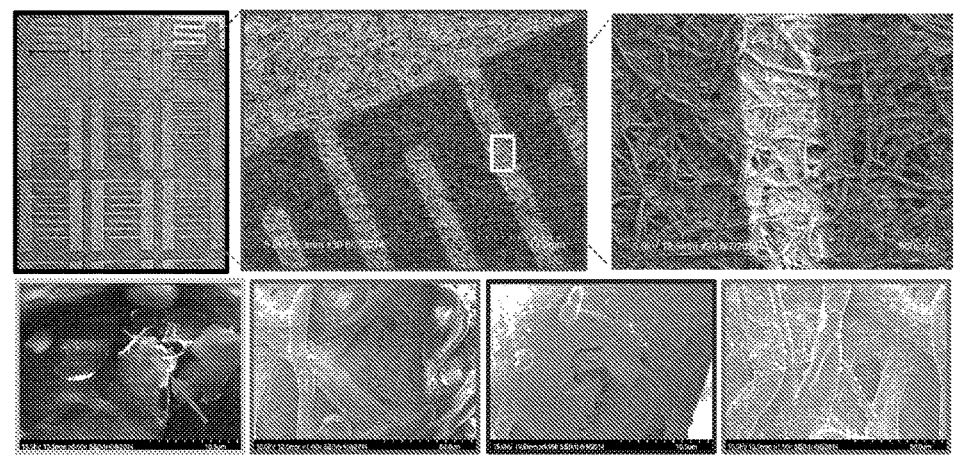
FIG. 2B. Schematic of biosensors and SEM images showing different components with loaded ascorbate oxidase.

The structural integrity of biosensor strip was also established by SEM imaging before and after immobilization of AO enzyme (FIG. 10D). The characteristic surface topography resembling 'flakes' type of biosensor without AO, (FIG. 2A) was significantly altered to 'thicker', denser coating pattern post immobilization with AO (FIG. 2B). A simple RC circuit (FIG. 10E) was used to measure the time it takes for a pin to get charged to a defined voltage value (63.2% of the maximum value), which corresponds to one time constant π=RC. By connecting a fixed capacitor and a variable resistor in an RC circuit, we used an I/O pin to measure the value of the variable resistor. The resistance reading was then displayed on the connected LCD monitor screen.

Surface characterization of biosensor strips revealed the variation in properties of strips with high and low density graphene platelet surface coatings and presence and absence of ascorbate oxidase to some extent. A clear difference in pattern was visible in representative areas using TEM (FIG. 10F-G). The study on elemental analysis with SEM/EDX (FIG. 10H-K) of biosensor strips shows abundance of gold (FIG. 10H), carbon (FIG. 10I), nitrogen (FIG. 10J) and oxygen (FIG. 10K). AFM analysis revealed the presence of polymer coated fibers on paper biosensor (FIG. 10L) and height profile of platelets across biosensor strip (FIG. 10M).

Computational Studies Regarding Specificity of the Biosensor

The human tear film is a complex three-layered structure comprising an outermost lipid layer, an aqueous layer and a mucus gel layer. The lipid layer mainly consist of cholesterol esters, and ester waxes; the aqueous layer mainly contains water (99%), proteins (lysozyme, lactoferrin, lipocalin, secretory IgA), electrolytes ($Na^+$, $K^+$, $Cl^-$, $HCO^-$, $Ca^{2+}$), and small molecules (ascorbic acid, glucose, lactate, uric acid and sialic acid). The main component of the mucus layer is mucin, which in turn is characterized by a polymeric assembly of units forming linear polyanionic molecules. Sialic acid is expressed in human tear film and is partly derived from mucin networks and is believed to provide the viscosity. Interestingly, sialic acid is a structurally similar molecule as compared to AA. To understand the disparity in interactions of sialic acid with AO as compared to that of AA to AO, a computational docking experiment was performed. Molecules of AA and sialic acid were sketched and minimized with MOE 2013.08. Force field: MMFF94, Cutoff: 8.10, Dielectric Constant: 1.00. Solvation method: distance model. 1AOZ was subjected to structural preparation before docking. MOE 2013.08 was utilized to perform the docking. Active sites were chosen with the residues Trp163, Trp36μ and His512. Induced Fit was chosen as the docking protocol. The Place method was triangle matcher. London dG was used as the scoring method. 30 docking poses were retained and the best scored pose was chosen as the docking pose. Molecular docking of AA and sialic acid to the binding pocket of AO (1AOZ) (FIG. 11A-D) revealed the following specific recognition events. First, in the AA docking pose, hydroxyl groups of the furan ring, other than that of the side chain, show more H-bond interactions with residues of the target. Then, in the sialic acid docking pose, there were no H-bond interactions between hydroxyl groups of the pyran ring and residues of the target. Instead, all H-bond interactions are exhibited between hydroxyl groups and carboxylic acid group of the side chain and residues of the target. From the H-bond distance difference between the two docking poses (FIGS. 11A and 11B), it can be determined that AA shows stronger H-bond interactions with residues of the target than with sialic acid. This shows that AA can be differentiated compared to sialic acid, which is present within the tear film and concentrations of AA can be accurately recorded without competitive inference from sialic acid. This contributes to the high specificity of the biosensor device. This study established the integral specificity of the biosensor coated with AO toward AA, minimizing the possibility of false positive results (specificity of 71% and false positive rate of ~6% was obtained in the preliminary testing).

Beyond computational docking studies, specific recognition of ascorbic acid on biosensor strip coated with ascorbate oxidase required experimental evaluations. Two other major components of aqueous humor, L-lactic and sialic acids, were chosen as competitors. UV-Vis spectroscopic studies were performed to achieve the selectivity. The integral absorbance of ascorbate oxidase was evaluated from its aqueous solution possessing 60 μg (20 U)/mL originated due to presence of aromatic side chains of some amino acids present in ascorbate oxidase (FIG. 11E-H). It was found that sequential addition of aliquots (1 μL; Final concentration 50μ) of L-ascorbic acid enhanced the absorbance value (Y) of ascorbate oxidase solution (FIGS. 11E and H) with a shift of $\lambda_{max}$ (x) from 280 nm to 267 nm indicating the loss of some aromaticity which might be occurring due to interaction of ascorbate oxidase with ascorbic acid. On the other hand, absorption spectrum of ascorbate oxidase with L-lactic acid (FIG. 11F) and sialic acid (FIG. 11G) did not reveal any significant change in either absorption level or $\lambda_{max}$ emphasizing the fact of selective interaction of ascorbate oxidase with L-ascorbic acid.

Layer by Layer Assembly of the Biosensor Device and Characterization by Raman Spectroscopy Raman spectroscopy was used to validate and optimize the layer by layer assembly of the biosensor device. The Raman spectrum of the biosensor surface showed the presence of D, G and 2D peaks (at 1340, 1582, and 2685 $cm^{-1}$, respectively) as clearly visible in FIG. 12A-D. With the subsequent polymer layer on the graphene platelet, the π-π interaction between graphene-polymer layers was manifested. Due to additional π-π interaction of graphene and polymer layer compared to graphene layers alone, more energy was required to vibrate the bonds, making it difficult to polarize the system. Therefore, the overall intensity decreases (bottom curve) after the formation of the polymer layer compared to without the polymer layer (top curve) as shown in FIG. 12A. Further evidence of π-π interaction was demonstrated in FIG. 12F. It is well known that the G band position shifts to lower frequency as the number of layers of graphene increases (FIG. 16B). FIG. 12F shows that the G band position is shifted from 1582 to 1579 $cm^{-1}$ due to the polymer layer, similar to the π-π interaction expected from graphene-graphene stacked layer. The 2D band splitting shown in FIG. 12E further confirms the stacking and π-π interaction due to polymer layer (the Lorentz curve fit to the G peak is shown in FIGS. 12G and 12H, corresponding to the curve with and without the grapheme polymer layers, respectively). With the subsequent layering of AO on top of the polymer layer, the Raman spectrum is affected due to interplay between 7-7 interaction of graphene-polymer and polymer-oxidase layers. The polymer-oxidase interaction lessens the effect of graphene-polymer interaction and hence the overall intensity rises (FIG. 12B: top curve) as compared to testing without the oxidase layer (FIG. 12B: bottom curve). FIG. 12C shows the result due to interaction between polymer-oxidase and oxidase-AA. The graphene-polymer interaction increases again due to oxidase-AA strong interaction. This leads to overall intensity decrease (FIG. 12C: bottom curve) after placing AA on the biosensor. The hypothesis that interaction of AA-AO leads to decrease of overall intensity of D, G, and 2D band, is tested by placing two different concentrations of AA on the graphene-polymer-oxidase layer. As expected, an increasing concentration of AA leads to a proportional decrease in the overall intensity of D, G and 2D band (FIG. 12D). The evidence of stacking of layers and π-π interaction is further confirmed by comparing the G band position, full-width-half-maximum (FWHM) of G band, and intensity ratio of D and G band ($I_D/I_G$) after each step (polymer, oxidase, AA, with/without serum) (see FIG. 16A). Polymer layer on graphene platelet creates more π bonds. This lowers the energy and increase Raman cross-section. Hence, G frequency decrease and G band intensity increases. Thus, $I_D/I_G$ ratio decreases. This is similar to decrease of G frequency with increase in number of graphene layers. From the same model, it predicts there will be ~3 additional layers after polymer is attached. The grain size of graphene decreases following the immobilization of AO on the polymer surface. This is evident by the increase in the FWHM of G band. This follows the Tuinstra-Koenig relationship $I_D/I_G$ inversely proportional to $L_a$, where $L_a$ is the grain size. Hence, it has been found that both G position and $I_D/I_G$ ratio increases. After reacting with AA, it creates a topological disorder in the graphene layer resulting in a loss of some of the aromatic rings for interaction. This weakens the non-covalent bonds and thereby $I_G$ increases and $I_D/I_G$ decreases. After reacting with serum and AA, it leads to more amorphization of the graphene layer. The $sp^3$ content of the system increases, which leads to increase of G frequency and decrease of $I_D/I_G$ ratio.

The interaction of AA with AO induces a charge transfer which leads to generation of carriers, and hence, to a modification of conductivity of the system. The enzymatic oxidation of ascorbic acid to dehydroascorbic acid in the presence of ascorbate oxidase produces two electrons; which will be transported through the conductive graphene oxide path to the electronic circuit to register the conductivity change (FIG. 12F). The enzyme ascorbate oxidase (AO), multi-copper enzyme, is chemically proteinase in nature with three various coordination sites. In step one, copper of the AO is bonded to two imidazole groups through the nitrogen and sulfur of cysteine. In step two, copper generates bond with two imidazole groups and in step three, histidines are bonded to every copper. The reaction mechanism of ascorbate oxidase with ascorbic acid in presence of oxygen is as follows:

AO (ox)+AA→AO (ox)·AA→AO (red)+P    (i)

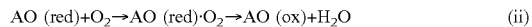

AO (red)+O$_2$→AO (red)·O$_2$→AO (ox)+H$_2$O    (ii)

In above two equations, AO (ox) and AO (red) are the oxidized and reduced states of the enzyme; AA is the ascorbic acid (substrate) and P is ascorbate free radical intermediate product. The change in potential can be attributed to the reduction of $Cu^{+2}$ to $Cu^{+1}$ on the enzyme. Because of the accumulated ascorbate ions on the surface of electrode, the electron density around the electrode changes; this in turn is detected by the transducer.

Analytical Performance of the Biosensor

Figure 8:
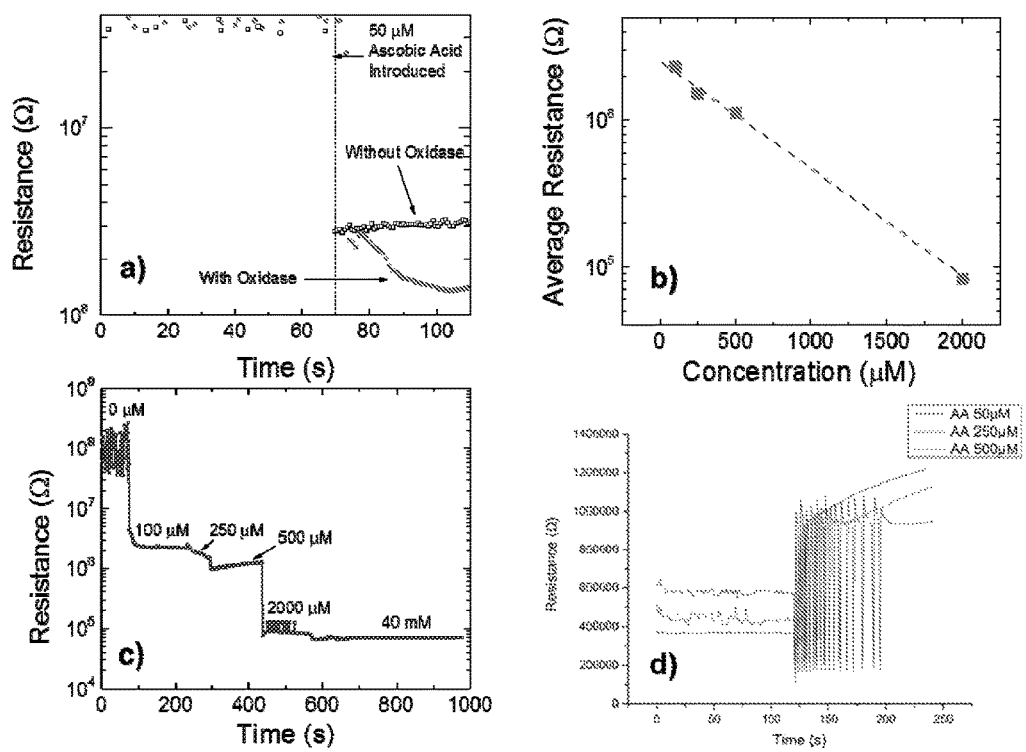
FIG. 8. Preliminary testing of a Typed biosensor showing concentration dependent resistance measurements (a-c); a calibration curve for measuring ascorbic acid (d).
Figure 9:
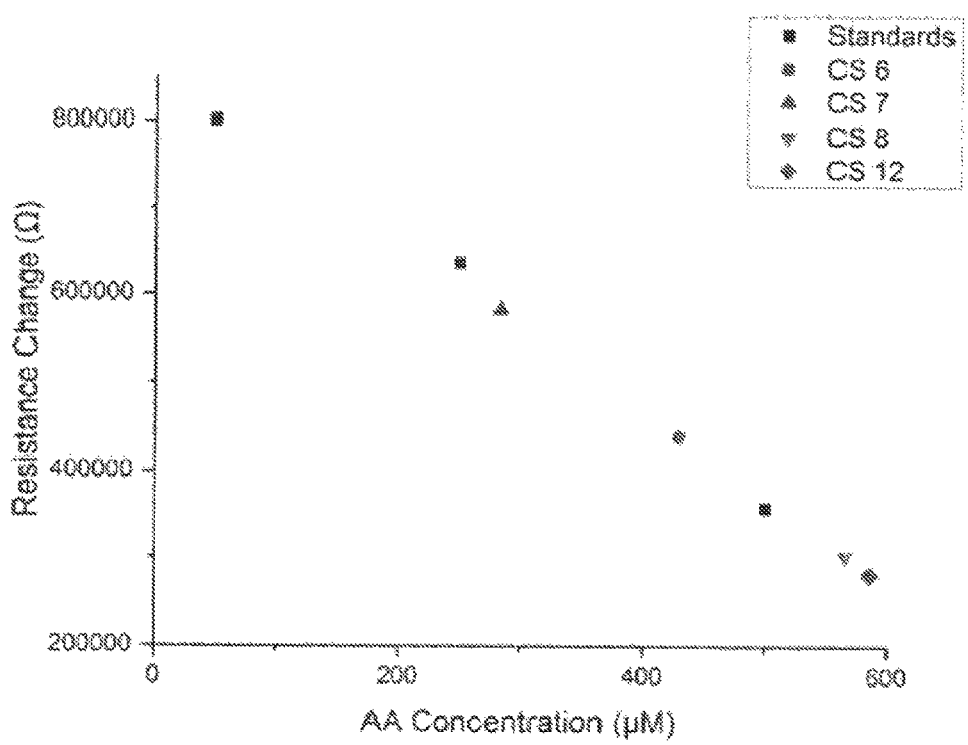
FIG. 9. Results of clinical samples plotted along with the standard ascorbic acid solution (black squares).

A calibration curve was generated by measuring the change of resistance of the biosensor with various known concentrations of AA placed in a standard solution of 0-40 mM concentration. Experiments were performed using AA standards with concentration of 0-40 mM. At low concentration of AA (<50 µM), the signal-to-noise ratio were not adequate to distinguish between presence and absence of AA. At 50 µM of AA, clear change of resistance was observed (FIG. 8A). Each concentration was tested by dropping 10 µL of solution on the biosensor. The resistance of the biosensor decreased with the increase in concentration of AA as shown in FIG. 13A. The corresponding calibration equation is plotted in FIG. 13D, where the data follows a linear trend ($R^2$=0.988). In order to measure the concentration of AA in an unknown sample, the measured resistances corresponding to the sample are compared to that of the calibration curve. Optimization of the biosensor was achieved with two different designs (FIG. 3). In one of the designs, a low concentration of graphene platelet was used (FIG. 3A). In the other design, a high concentration of graphene platelet was used (FIG. 3B). The graphene platelet formed a largely unconnected system leading to high surface resistance (>6 MΩ) below the percolation threshold as shown in FIG. 13B (CS#1-3; CS: Clinical Sample). When the concentration of graphene platelet was raised above the percolation threshold, a connected system was formed (FIG. 13B, CS#4) leading to lower surface resistance (<0.2 MΩ). These two systems led to two different behaviors for the graphene platelet-AO assembly and with subsequent interactions of AA. For example, the system shown in FIG. 13B (CS#1-3) leads to a decrease of surface resistance due to the presence of ionic solutions like AA (this results from the formation of conductive channels between the graphene platelet islands). In comparison, the system showed in FIG. 13B (CS#4) leads to an increase of surface resistance due to the product formation of catalyzed reaction between AO and AA, FIG. 13C shows the Box-and-Whisker plots of the AA concentration from samples of human aqueous humor obtained from subjects who underwent therapeutic anterior chamber paracentesis (n=12) using the biosensor and standard colorimetric assay (see the Methods section for the process of aqueous humor collection). The boxes show median and quartiles, where whiskers are corresponding to $5^{th}$ and $95^{th}$ percentiles. Levene's test was performed to quantify the homogeneity of variance. The results (F=9.45, P=0.0055) showed that the population variance are significantly different at 0.05 level (also shown in FIG. 13C). One way ANOVA testing of the population of the biosensor and colorimetric assay (n=12) showed that (F=0.113, P=0.74), at 0.05 level the population means were not significantly different. Tukey test also confirmed the above finding indicating that the difference of means between the biosensor and colorimetric assay are not significantly different at 0.05 level. Finally, the t-test (P=0.678) showed no statistical difference exist between the mean obtained from two methods.

The Biosensor Device Comparison to Calorimetric Assay

The validation of the results for the aqueous humor clinical samples was performed by obtaining the concentration through standard colorimetric assay and comparing them to the mass spectrometric based analytical methods. The AA concentration was first determined by a coupled enzyme reaction (AA Assay Kit, Sigma-Aldrich, MAK074), which results in a colorimetric ($\lambda_{abs}$=570 nm)/fluorometric ($\lambda_{ex}$=535/$\lambda_{em}$=587 nm) product, which was proportional to the AA present. Total volume of 200 µL (10 µL of AA, 50 µL of master mix, 140 µL of buffer) with AA concentration ranging from 0-10 nmol/well was used to generate the standard curve. To measure the concentration of AA in the clinical samples, 10 µL of clinical sample was added to the master mix and buffer (200 µL) to obtain the absorbance/fluorescence data. The concentration of AA was obtained by comparing the absorbance or fluorescence data to the calibration curve generated for the AA standard solution. The comparison between the results obtained from two methods is shown in FIG. 13E. The regression analysis showed strong agreement between the two methods ($R^2$=0.89, Pearson's R=0.95).

Bland-Altman analysis was performed to measure the agreement between two quantification methods of AA: colorimetric assay and the biosensor (FIG. 13F). Bland-Altman plot was obtained by plotting the difference between concentrations measured from two methods (biosensor and colorimetric assay) with the mean of the concentrations measured by the two methods. It generated a bias value of −56.5 µM, which indicates that the biosensor under predicted the AA concentration compared to the colorimetric assay. This may be due to the oxidation of AA during sample handling and experimentation. The limit of agreement (95% confidence interval, CI) was calculated by taking 2×SD of the difference value. Bland-Altman plot was obtained from 12 samples (n=12) analyzed on the biosensor and the colorimetric assay with correlation R=0.7761 (P<0.01), slope=−1.045 (P<0.01), and intercept=1219.3 (P=0.005). The Pearson coefficient represents the linear relationship between the two methods of concentration measurement from the biosensor and colorimetric assay. Its value ranges from [−1, 1], with 1 representing the perfect correlation of the two methods. The Pearson R=0.95 with intercept set at 0. P<0.01 rejected the null hypothesis that there is no correlation between the biosensor and colorimetric assay measurements.

Further statistical analysis was performed to construct the Receiver Operating Curve (ROC). The detection of AA using the biosensor has an accuracy of 81.3%, sensitivity of 88.9% [95% confidence interval (CI), 62-100%] and specificity of 71.4%. ROC shows the area under the curve of 0.94 for AA detection. (FIG. 4G) The clinical data were analyzed using 6-point rating scale (defined by numbers 1-6) by comparing the results obtained from the biosensor, colorimetric assay and high resolution mass spectroscopy (HR-MS). The following category of classification was followed to construct the ROC. 1: Definitely negative [MS (N), Colorimetric (N), The biosensor (N or low)]; 2-Probably negative [MS (N), Colorimetric(N), biosensor (Y or High)]; 3-Possibly negative [MS (N), Colorimetric (Y), biosensor (N or Low)]; 4-Possibly positive [MS (Y), Colorimetric (N), biosensor (Y or High)]; 5-Probably positive [MS (Y), Colorimetric (Y), biosensor (N or Low)]; 6-Definitely positive [MS (Y). Colorimetric (Y), biosensor (Y or High)]

AA Confirmation Using Mass Spectrometer

The presence of AA in the clinical sample was confirmed by liquid chromatography (LC) followed by high-resolution mass spectrometry (HR-MS) as shown in FIG. 14A-B. The AA in the clinical sample was converted to a charged (ionized) state, with subsequent analysis of the ions and any fragment ions that are produced during the ionization process, was performed on the basis of their mass to charge ratio (m/z). The characteristic AA fragment is obtained at m/z of 175.024 (denoted by an arrow). The same peak is also seen in all the clinical samples (denoted by arrow) confirming the presence of AA in the clinical samples.

CONCLUSION

The methods and compositions of the invention can replace the subjective Seidel test that is currently the gold standard for evaluating aqueous humor leaks. This will offer many advantages to the ophthalmology community. The methods and compositions will be a game changer for the evaluation of post-surgical incisions from glaucoma filtering procedures (such as trabeculectomies) as well as for anterior ocular trauma patients.

It has been shown that ascorbic acid concentrations in the tear film are connected to release of the antioxidant from the lacrimal gland with tear film production and do not come from leaking of the molecule through the cornea in normal healthy eyes. This is the first use of ascorbic acid as a biomarker for a corneal injuries and other eye conditions.

In a research sense, the biosensor offers a reliable, objective standard for grading the degree of a wound leak, which could be used to stratify wounds leaks into categories based on severity, with higher severity leaks seen in cases of higher AA concentration in the tear film. This will provide researchers with a reproducible way for monitoring post-operative outcomes and could replace alternative methods that are currently used.

Finally, this reliable technology would also be able to revolutionize post-operative management in remote areas or third world countries where access to specialist is limited. In these situations the biosensor can be used by health care aids to monitor post-operative patients and used to help in the decision of whether initiation of antibiotics is needed. The biosensor will provide critical diagnostic information care providers in order to initiate sight-saving treatments.

In summary, eye conditions, including for example, a full-thickness laceration in the cornea or anterior scleral from trauma or incisional surgery releases aqueous humor into the tear film, which pathologically increases the concentration of tear film AA to a measurably higher level than that found in normal eyes. Ascorbic acid can also be released into the tear film from perforations in the cornea or anterior scleral from infections or ulcers. This level can be detected with the use of the methods and compositions of the invention. The results from the biosensor can be used as a surrogate biomarker of the integrity of anterior ocular wounds and eye conditions. This is the first time that ascorbic acid has been identified as a biomarker for ocular disease or injury. Current methodologies of absorption and fluorescence based detection are not effective because they have low sensitivity and consume too much time to be clinically relevant in emergency settings. Biosensors of the invention offer electrical resistance measurement based technique that provides an effective and efficient method for testing AA in a POS delivery system. Biosensors of the invention can accurately and quantitatively measure AA levels in in vitro testing of aqueous humor samples collected from human subjects. The clinical samples from human aqueous humor were successfully tested to determine the concentration of AA. Complimentary analytical methods such as colorimetric assay and mass spectrometry were utilized to compare and confirm the presence of particular concentration of AA in the clinical samples. The biosensor can be refined to make improvements in the specificity and sensitivity in order to use this biosensor in a clinical setting by a vast array of health care providers. The methods and compositions of the invention provide a significant change in the current method for evaluating eye post-surgical patients as well as trauma patients. It will improve the utilization of health care resources and quality of care of patients.

The invention claimed is:

1. A biosensor for the detection of an analyte, the biosensor comprising: a layer comprising a mixture of graphene nanoplatelets and one or more polymers, wherein the polymers are amphiphilic block copolymers, a layer of a ligand for the analyte in contact with hydrophilic blocks of the amphiphilic block copolymers; at least one sensor electrode; and a substrate.

2. The biosensor of claim 1, wherein the at least one sensor electrode is between the layer comprising a mixture of graphene nanoplatelets and one or more polymers and the layer of a ligand for the analyte.

3. The biosensor of claim 1, wherein the analyte is ascorbic acid and the ligand for the analyte is ascorbate oxidase.

4. The biosensor of claim 3, wherein the ascorbate oxidase is present at a concentration at about 3 to about 100 U/cm$^2$.

5. The biosensor of claim 1, wherein the substrate is selected from one or more of filter paper, acrylamide, cellulose, nitrocellulose, glass, silicon wafer, indium tin oxide, mica, polystyrene, or polyvinylidene fluoride (PVDF) filter, glass fiber filters, fiberglass, polyethylimine coated glass fiber filters, porous mylar, transparent porous film, cellulose nitrate (CN) membrane, mixed cellulose ester membrane, cellulose acetate membrane, polyethersulfone (PES) membrane, PTFE membrane, ultrafiltration membranes of poly(vinyl chloride) (PVC), carboxylated poly (vinyl chloride) (CPVC), polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids.

6. The biosensor of claim 1, wherein the one or more polymers is poly(styrene) block-poly (acrylic acid) (PS-b-PAA).

7. The biosensor of claim 1, further comprising a fluidics chamber.

8. The biosensor of claim 1, further comprising a cover.

9. A method of using the biosensor of claim 1 for detecting an analyte in a sample comprising contacting the biosensor with the sample and detecting the analyte with a detector.

10. The method of claim 9, wherein the detector detects binding or interaction of the analyte and the analyte ligand due to a change in electrical resistance caused by binding or interaction of the analyte in the sample with the analyte ligand; due to a change in mass on the biosensor; due to a colorimetric change; due to a fluorescent reaction; due to a change in a Raman spectroscopy reading; due to a change in a Fourier transform infrared spectroscopy reading, due to a change in a mass spectrometry reading, or due to electrochemical changes.

11. The method of claim 9, wherein the sample is tears, tear film, aqueous layer of the tear film, aqueous humor, sweat, blood, serum, plasma, urine, saliva, or other bodily fluids.

12. A method of using the biosensor of claim 1 for detecting an analyte in a sample, comprising contacting a sample with the biosensor, and inserting the biosensor into or onto a device comprising a detector to measure change in electrical resistance, and a screen for visualizing the change in resistance, thereby detecting an analyte in the sample.

13. The method of claim 12, wherein the amount of the analyte in the sample is detected.

14. A method of using the biosensor of claim 1 for diagnosing an aqueous humor leak, comprising contacting the biosensor with a tear, tear film, aqueous layer of the tear film, or aqueous humor sample of a subject, detecting an amount of an analyte in the sample, and diagnosing an eye condition in the subject where the concentration of the analyte in the sample is elevated as compared to a control sample or control standard.

15. A method of using the biosensor of claim 1 for diagnosing an eye condition in a subject comprising contacting the biosensor with a tear film sample of a subject, detecting an amount of ascorbic acid in the tear film sample from the subject and diagnosing an eye condition in the subject where the amount of ascorbic acid is elevated as compared to a control standard or control sample.

16. The method of claim 14, wherein the analyte is ascorbic acid.

17. A device comprising a biosensor comprising a layer comprising a mixture of graphene nanoplatelets and one or more polymers, wherein the polymers are amphiphilic block copolymers, a layer of a ligand for an analyte in contact with hydrophilic blocks of the amphiphilic block copolymers; at least one sensor electrode; a substrate; and a detector connected to a data acquisition system.

18. The device of claim 17, wherein the detector is a multimeter.

19. The device of claim 17, wherein the data acquisition system is selected from the group consisting of a computer, a hand-held device, a cell phone, and a tablet.

20. The device of claim 17, further comprising a screen that allows for visualization of an amount of analyte present in a sample.

* * * * *